United States Patent
Nahaliel et al.

(10) Patent No.: US 6,243,438 B1
(45) Date of Patent: Jun. 5, 2001

(54) MULTI-SLICE DETECTOR ARRAY

(75) Inventors: Ehud Nahaliel, Lower-Galilee; Ehud Dafni, Caesarea; Andre Feldman, Haifa; David Ruimi, Netanya; David Freundlich, Haifa, all of (IL)

(73) Assignee: Marconi Medical Systems Isreal Ltd., Haifa (IL)

( * ) Notice: Subject to any disclaimer, the term of this patent is extended or adjusted under 35 U.S.C. 154(b) by 0 days.

(21) Appl. No.: 09/242,079

(22) PCT Filed: Aug. 6, 1997

(86) PCT No.: PCT/IL97/00267

§ 371 Date: Feb. 4, 1999

§ 102(e) Date: Feb. 4, 1999

(87) PCT Pub. No.: WO98/05980

PCT Pub. Date: Feb. 12, 1998

(30) Foreign Application Priority Data

Aug. 7, 1996 (IL) .................................................... 119033

(51) Int. Cl.[7] .................................................. G01N 23/00
(52) U.S. Cl. ............................... 378/19; 378/4; 378/207
(58) Field of Search ............................... 378/4, 19, 207; 250/370, 367, 445.033

(56) References Cited

U.S. PATENT DOCUMENTS

| 4,255,659 | * | 3/1981 | Kaufman | 250/370 |
|---|---|---|---|---|
| 4,292,524 | * | 9/1981 | Albrecht et al. | 250/445.003 |
| 4,292,538 | * | 9/1981 | Carlson | 250/367 |
| 4,417,354 | | 11/1983 | Pfeiler . | |
| 4,697,280 | * | 9/1987 | Zarnstorff et al. | 378/207 |
| 4,965,726 | * | 10/1990 | Heuscher et al. . | |
| 5,166,961 | * | 11/1992 | Brunnett et al. | 378/19 |
| 5,241,576 | | 8/1993 | Lonn . | |
| 5,430,784 | | 7/1995 | Ribner et al. . | |
| 5,469,486 | * | 11/1995 | Hu et al. | 378/4 |
| 5,493,593 | | 2/1996 | Muller et al. . | |
| 5,768,331 | * | 6/1998 | Gordon et al. | 378/19 |

FOREIGN PATENT DOCUMENTS

| 0 429 977 | 6/1991 | (EP) . |
|---|---|---|
| 0 429 977 A3 | 6/1991 | (EP) . |

* cited by examiner

Primary Examiner—David V. Bruce
Assistant Examiner—Pamela R. Hobden
(74) Attorney, Agent, or Firm—Fenster & Company Patent Attorneys, Ltd.

(57) ABSTRACT

Apparatus for producing multiple image slice data responsive to incident radiation passing through an object. The apparatus includes a detector array having a plurality (p) of parallel rows of detector elements which receive such incident radiation and generate signals therefrom, each of which rows is characterized by a width measured prior to collimation in the direction perpendicular to a long dimension thereof; and signal processing circuitry which receives signals from the detector elements and which combines the signals in a first combination mode and in at least m additional combination modes. In the first combination mode, the circuitry forms a set of n groups of rows, each such group of rows having an effective group width substantially equal to the effective group width of each of the other groups in the set. In each of the m additional combination modes, the circuitry forms different sets of n groups of rows, each such set having a different effective group width common to all groups in the set.

65 Claims, 18 Drawing Sheets

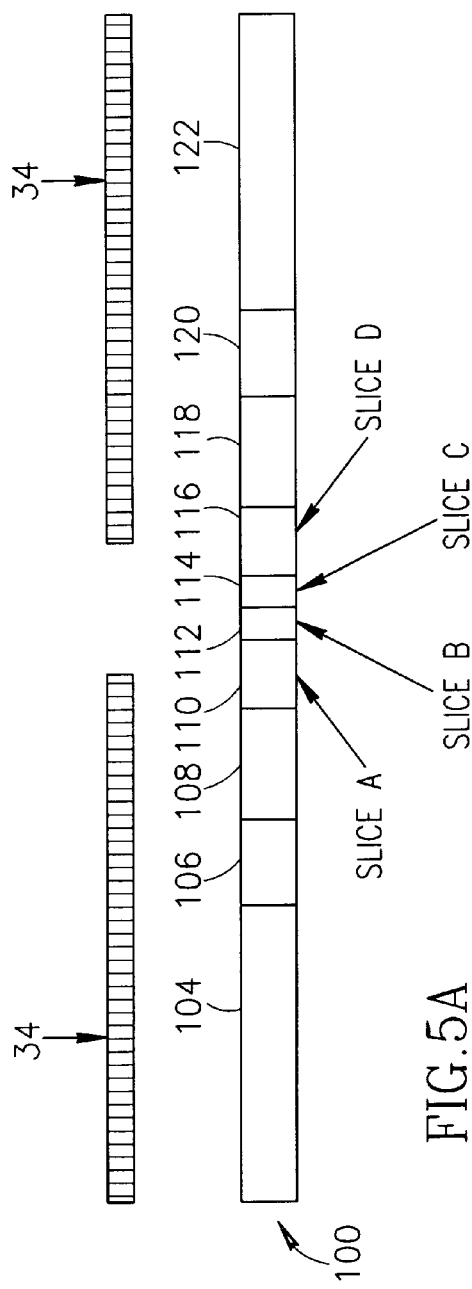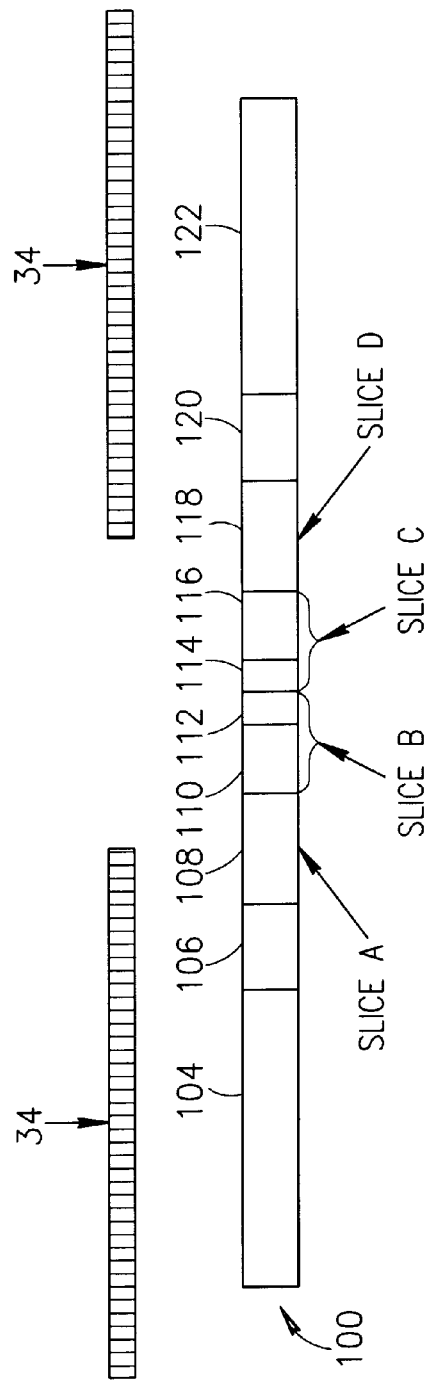

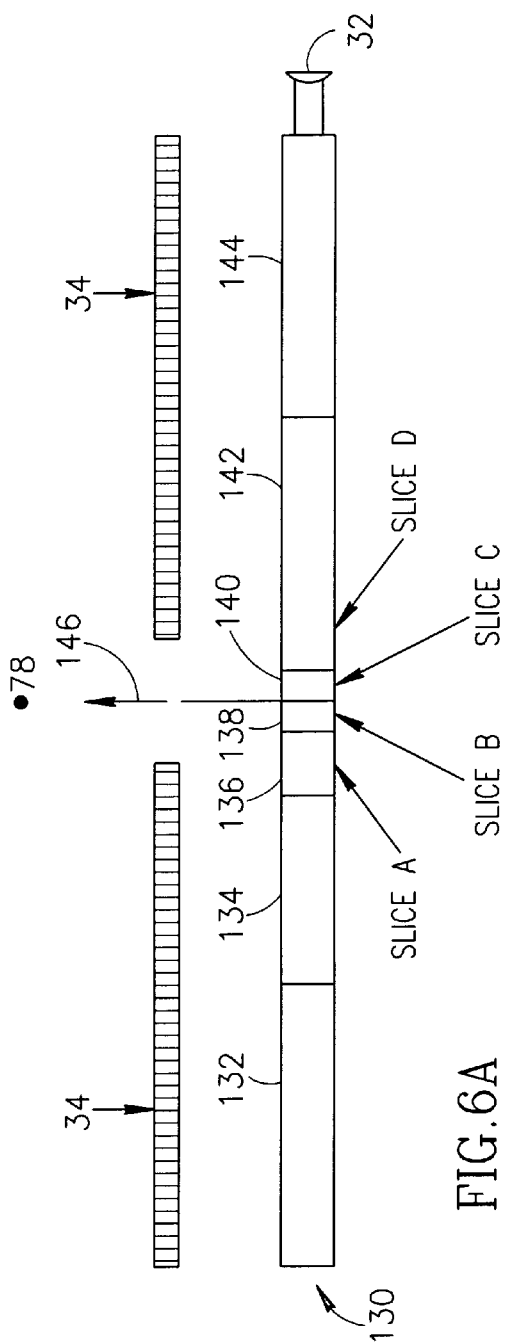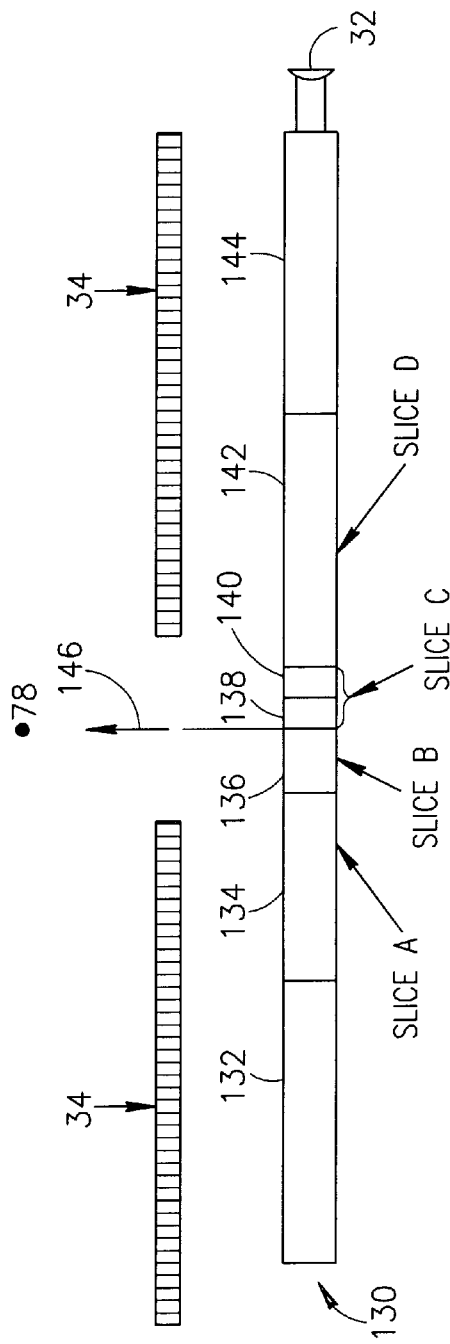
FIG.6A
FIG.6B

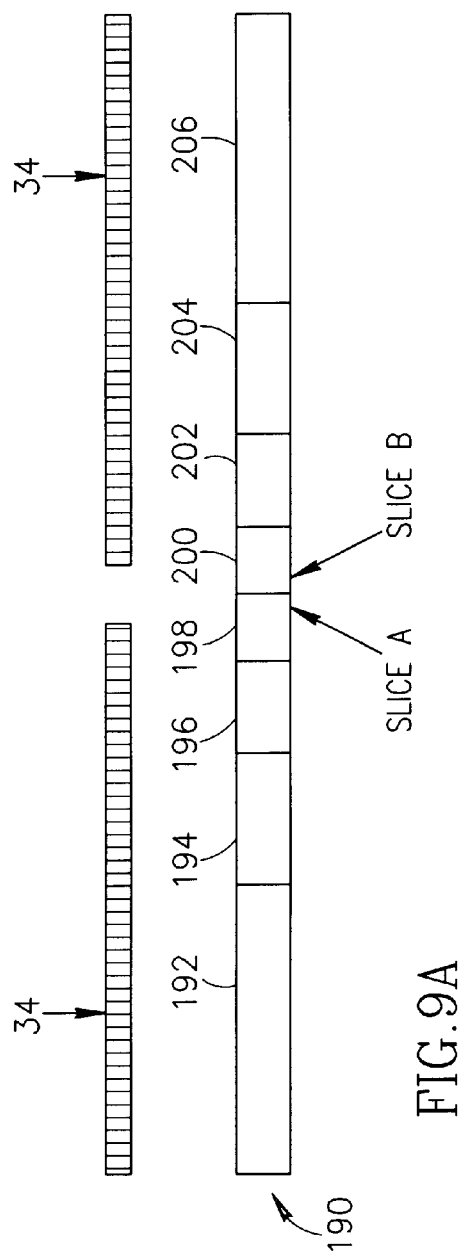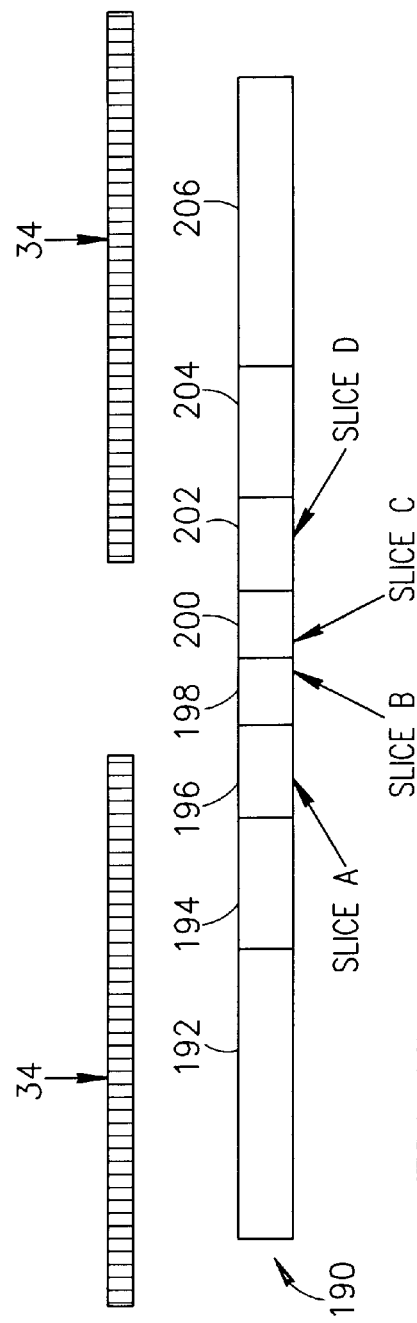

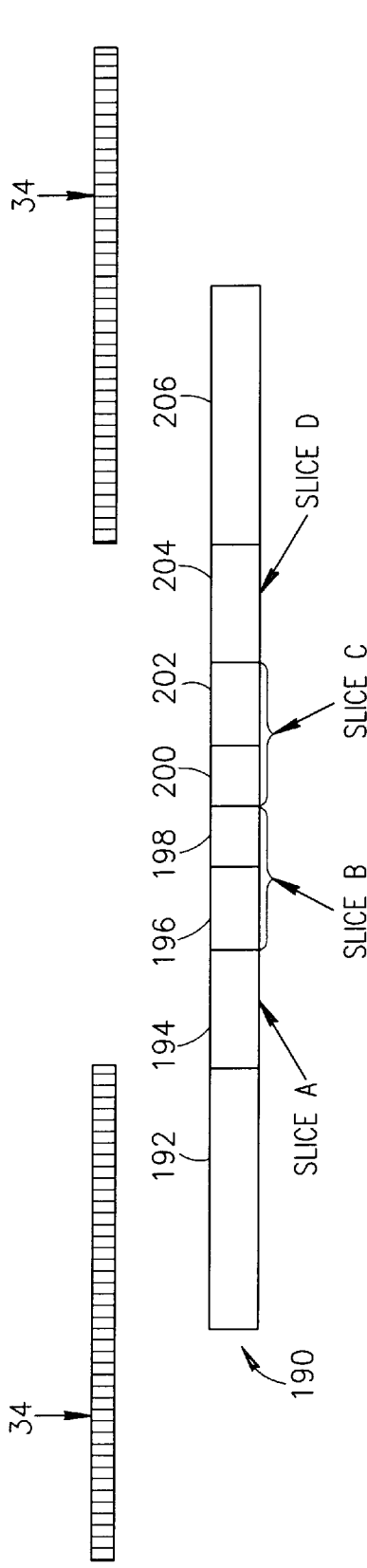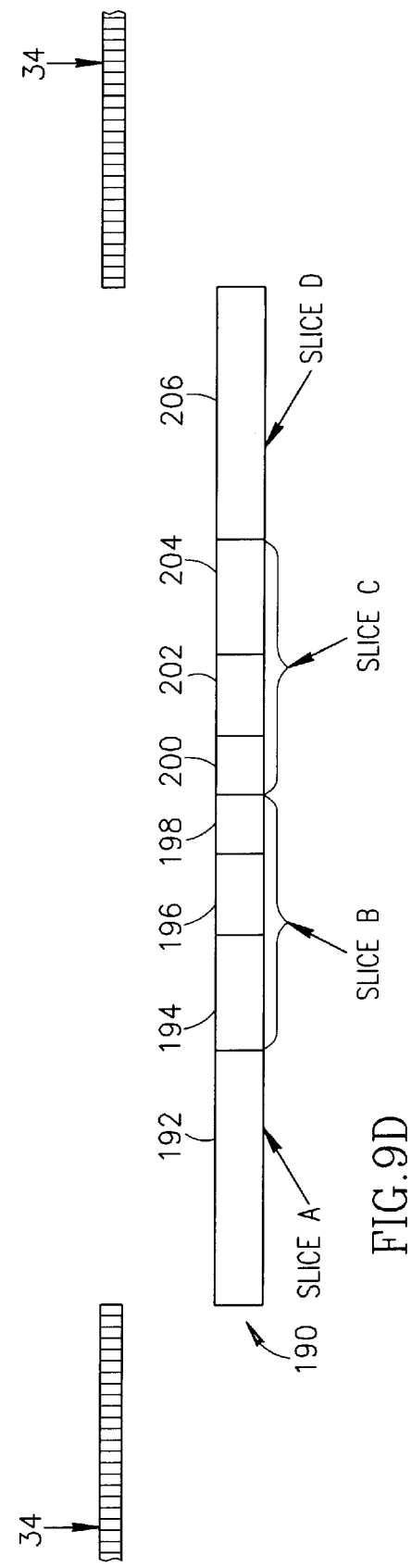

MULTI-SLICE DETECTOR ARRAY

FIELD OF THE INVENTION

The present invention relates generally to transmission computerized tomographic (CT) systems, and specifically to segmented array detectors for use in such systems to simultaneously acquire data from multiple axial slices.

BACKGROUND OF THE INVENTION

CT scanning systems and methods are well known in the art, particularly for medical imaging and diagnosis, but also in other field of imaging, for example, industrial quality control.

CT scanners generally create images of one or more sectional slices through a subject's body. A radiation source, such as an X-ray tube, irradiates the body from one side thereof. A collimator, generally adjacent to the X-ray source, limits the angular extent of the X-ray beam, so that radiation impinging on the body is substantially confined to a planar region defining a cross-sectional slice of the body. At least one detector (and generally many more than one detector) on the opposite side of the body receives radiation transmitted through the body substantially in the plane of the slice. The attenuation of the radiation that has passed through the body is measured by processing electrical signals received from the detector.

Typically, in commonly-used third- and fourth-generation CT scanners, the X-ray source (or multiple sources) is mounted on a gantry, which revolves about a long axis of the body. In third-generation scanners, the detectors are likewise mounted on the gantry, opposite the X-ray source, while in fourth-generation scanners, the detectors are arranged in a fixed ring around the body. Either the gantry translates in a direction parallel to the long axis, or the body is translated relative to the gantry. By appropriately rotating the gantry and translating the gantry or the subject, a plurality of views may be acquired, each such view comprising attenuation measurements made at a different angular and/or axial position of the source. Commonly, the combination of translation and rotation of the gantry relative to the body is such that the X-ray source traverses a spiral or helical trajectory with respect to the body. The multiple views are then used to reconstruct a CT image showing the internal structure of the slice or of multiple such slices, using methods known in the art.

The lateral resolution of the CT image, or specifically, the thickness of the slices making up the image, is generally determined by the angular extent of the radiation beam or of the individual detectors, whichever is smaller. The use of thick slices is advantageous in increasing the signal/noise ratio, and thereby reducing the time needed to acquire the data needed to reconstruct an image. But images reconstructed using thick slices have poor resolution in the axial direction and are more susceptible to partial volume artifacts, i.e., imaging errors that are introduced when a single volume element (voxel) within a slice contains two types of tissue having different attenuation coefficients.

Smaller detectors are generally used, therefore, to improve axial resolution and reduce partial volume artifacts. Excessive reduction of the extent of the detector, however, leads to degradation of the signal/noise ratio and decreases the throughput of the imaging system. Using very small detectors can also reduce the system's dose efficiency, i.e., increase the relative amount of radiation to which the portion of the body being imaged is exposed, because the angular extent of the X-ray beam irradiating the body will typically extend somewhat beyond the bounds of the detectors. Radiation outside these bounds is "wasted," since it is not used in forming the CT image.

In order to improve throughput, as well as increase axial resolution and utilize the X-ray source more efficiently, various inventors have described the use of differently configured detector arrays. Such arrays typically include a plurality of radiation detectors, such as scintillator-photodiodes, which receive radiation simultaneously from a radiation source and are thereby used to acquire multiple views and/or multiple slices simultaneously. Spiral modes of translation and rotation, as mentioned above, are frequently combined with multi-slice image acquisition to cover a greater volume of the body in less time with improved axial resolution.

For example, U.S. Pat. No. 4,965,726, to Heuscher, et al., whose disclosure is incorporated herein by reference, described a CT scanner with a plurality of segmented detector arrays. Each array includes a plurality of rows of radiation-sensitive cells. The rows may have different dimensions in a lateral direction, perpendicular to the long dimension of the rows, and the effective lateral dimensions of the rows may be varied by moving collimators adjacent thereto, so as to provide slices of the same or different lateral thicknesses. Multiple detectors may be grouped together in the lateral direction to provide thicker slices, so as to improve the signal/noise ratio and throughput of the scanner, while reducing partial volume artifacts relative to slices of comparable thickness that are acquired using a single detector having an equivalent lateral dimension.

U.S. Pat. No. 5,241,576, to Lonn, whose disclosure is likewise incorporated herein by reference, similarly describes a CT scanner including an array of detector elements for the purpose of acquiring thick-slice images with reduced partial volume artifacts. The array includes a plurality of detector elements, wherein each such element includes a set of sub-elements disposed along the slice thickness (lateral) dimension. The signal output of each sub-element is processed individually, generally by taking the log of the signal and applying a weighting factor thereto. The processed outputs of the plurality of sub-elements belonging to a single element are then summed together to form a combined thick-slice signal.

U.S. Pat. No. 5,430,784 to Ribner, et al., whose disclosure is also incorporated herein by reference, describes a CT scanner and detector array having a plurality of rows of identical detectors, which are connected together by a controllable switching matrix. This switching matrix is controlled to interconnect a predetermined number of successive detector sub-elements, in order to produce combined signals corresponding to one or more slices of a desired thickness.

U.S. Pat. No. 4,417,354, to Pfeiler, whose disclosure is incorporated herein by reference, describes a CT scanner including a detector array that is mounted to pivot about a lateral axis, perpendicular to an image slice acquired by the array. The array is pivoted in order to increase the effective resolution within the image slice, but only a single image slice is provided, and no suggestion is made of changing the slice thickness by pivoting the array about a transverse axis.

Similarly, U.S. Pat. No. 5,493,593, to Müller et al., whose disclosure is incorporated herein by reference, describes a scanner for CT microscopy including a tiltable detector array, which is also shifted horizontally in order to maximize the utilization of the array. Only a single image slice is provided, however, without suggestion of changing the slice thickness.

SUMMARY OF THE INVENTION

It is an object of the present invention to provide detector arrays for simultaneous acquisition of multiple image slices of variable thickness. Preferably, at a given time all the slices are of substantially equal thickness, and the thickness may be accurately and conveniently controlled.

In one aspect of the present invention, the thickness is controlled in successive steps of increasing thickness.

In another aspect of the present invention, the number of switching and summation elements needed for combining adjacent elements of such detector arrays to form slices of a desired thickness is minimized.

In another aspect of the invention, the outputs of the elements are combined to provide slices of variable thickness. Preferably, one or two thick slices are provided together with one or two thin slices wherein the ratio between the thickness of the two types of slices is greater than 2:1, more preferably, greater than 3:1 and most preferably greater than 5:1. In a preferred embodiment of the invention, the ratio of the thicknesses is 9:1 or 10:1.

Preferably, the detector arrays comprise radiation detectors and are used in CT scanner systems.

In preferred embodiments of the present invention, a detector array, for use in an imaging system, comprises a plurality of rows of detectors, each row characterized by a width in a lateral dimension perpendicular to the long axis of the row, which long axis is typically aligned in the imaging system in a generally circumferential direction relative to a body being imaged. The detectors in each row receive radiation from a corresponding slice of an object being imaged and generate signals in response to the radiation. Preferably the array includes rows having different widths, more preferably at least four different widths. A minimum slice thickness is defined by a lateral dimension of a slice, i.e., a dimension of a slice measured in a direction parallel to the lateral dimension of the rows, corresponding to a row of the array having the smallest width. Switching circuitry associated with the array selectively combines signals generated by adjacent detectors in different rows, so as to produce sum signals corresponding to multiple slices having a common thickness, which is a selectable value equal to or greater than the minimum slice thickness.

Preferably the switching circuitry produces sum signals corresponding to at least four laterally-adjacent, substantially contiguous slices, all of which have a common thickness. Acquiring multiple, contiguous image slices simultaneously, as described herein, generally increases the throughput and/or resolution of the imaging system. In general, multi-slice imaging also increases the dose efficiency of the system, i.e. reduces the relative amount of radiation to which the body is exposed in producing a CT image, particularly when thin image slices are acquired, since using multiple rows of detectors reduces the relative amount of "wasted" radiation falling outside the bounds of the detectors.

In preferred embodiments of the present invention, the switching circuitry may combine the signals using any appropriate circuit elements and computational algorithms known in the art. Preferably, the signals undergo a log operation, as is known in the art, and are digitized and summed. However, other suitable operations may similarly be used, and the order of performing the operations may be varied, as desired to reduce the cost and/or number of components in the imaging system, subject to the requirement that the system produce images of a desired quality. It will be understood that image quality includes measures of resolution, signal/noise ratio, artifacts, particularly partial volume artifacts, and other measures known in the art.

In some preferred embodiments of the present invention, the detector array comprises four adjacent central rows, having a common lateral width, which is the smallest width of rows in the array, and a plurality of peripheral rows, symmetrically arranged on both sides of the four central rows. The widths of the peripheral rows are preferably integer multiples of the width of the central rows, wherein the widths of the rows preferably generally increase with the lateral distance of the rows from the central rows.

In some preferred embodiments of this type, the fifth and sixth rows, which are peripherally adjacent to the four central rows on either side thereof, have a common width generally twice that of the central rows. The seventh and eighth rows, which are peripherally adjacent to the fifth and sixth rows, respectively, have a common width generally twice that of the fifth and sixth rows. Ninth, tenth and additional pairs of rows, if desired, are similarly added peripherally as desired, each additional row having width generally twice that of its inner neighbor.

In accordance with such preferred embodiments, when four slices of the minimum thickness are desired, switching circuitry selects signals only from the four central rows. To produce four slices of a greater thickness, approximately twice the minimum thickness, the switching circuitry selects signals from the fifth and sixth rows to produce two such slices, and combines signals generated by mutually adjacent first and second rows of the four central rows and by mutually-adjacent third and fourth rows thereof, to produce two more such slices. To produce four slices of approximately four times the minimum thickness, the switching circuitry selects signals from the seventh and eighth rows to produce two such slices, and combines signals from the first, second and fifth rows (the fifth row being adjacent to the first row) to produce a third such slice, and from the third, fourth and sixth rows to produce a fourth slice. Four slices of thickness corresponding to the width of any of the rows of the array, up to the largest such width, may similarly be produced.

In this and other preferred embodiments of the present invention, the slice thicknesses are generally measured at the location of the object being imaged. These thicknesses depend primarily upon the width of the corresponding row or combined rows of detectors, but are also affected by other elements of the imaging system in which the detector array is used. Such elements typically include a radiation source and beam-control optics, such as collimator slits. Therefore, while the slice thicknesses are approximately proportional to the row widths, other aspects of the system must be taken into account to determine the slice thicknesses accurately.

Thus, in the context of the present invention, it will be understood that the use of the term "substantially" or "approximately" in stating a detector width dimension, for example to say that the width of rows of detectors are substantially equal, or that the thickness of one row is substantially an integer multiple of another row, means that the detector thickness is such that the slices traversed by the radiation beam has approximately the stated dimension or ratio. This includes any correction to the detector width which might be required, for example to correct for the difference between the effective thickness $a_{eff}$ and the thickness that would be obtained if focal point 78 were infinitesimal or for other geometrically caused variation between the effective slice width and the detector width. Such correction is generally very small compared to the detector and slice dimensions of interest.

It will be appreciated that the preferred embodiments described above allow a wide range of choices of slice thickness to be produced by the detector array and switching circuitry, relative to the number of rows in the array. For example, an array having ten rows of detectors, in accordance with a preferred embodiment of the present invention of the type described above, will be capable of producing four slices having a common thickness, which is variable from a minimum slice thickness up to a maximum thickness approximately eight times the minimum slice thickness. By comparison, an array composed of rows of detectors having equal row widths would require 32 rows of detectors in order to produce such an 8:1 range of slice thicknesses, and would also require considerably more complex and costly switching circuitry to accomplish this purpose. In other, analogous preferred embodiments of the present invention, arrays having greater or lesser numbers of rows may be used to similar advantage.

Furthermore, in the preferred embodiments of the present invention described above, the selection of slice thicknesses is accomplished without the use of any additional mechanical aperture, collimator or beam optics.

In other preferred embodiments of the present invention, however, a linear aperture whose width is variable in a lateral direction, i.e., the direction parallel to the lateral dimension of the rows of the array, is used in conjunction with the detector array and switching circuitry to produce slices having desired thicknesses. In one preferred embodiment of this sort, two central rows of the array have the smallest width, and peripheral rows having greater widths are symmetrically arranged on both sides of these two central rows. The aperture is constructed and aligned so that when it is fully open, all rows of the array are exposed to radiation from the object. When the aperture is narrowed, however, it masks all or portions of successive peripheral rows in the array, preventing radiation from impinging thereon. The aperture thus controls the effective widths of the peripheral rows by covering or exposing desired portions thereof.

Signals from mutually-adjacent detectors in different, selected rows of the array are combined by the switching circuitry, as described above, to produce multiple image slices having a common, desired thickness. By appropriately varying the aperture from a minimum to a maximum opening dimension, while controlling the switching circuitry, the thickness of the multiple slices is increased approximately by multiples of the minimum slice thickness, as defined by the smallest row width and/or minimum aperture. The addition of the aperture allows a wider variety of thickness multiples to be produced, for a given number of rows, than in the preferred embodiments described above in which only the detector array and switching circuitry are used to determine the slice thicknesses.

In some preferred embodiments of the present invention, the linear aperture may be narrowed sufficiently to mask all peripheral rows of the array and portions of the two central rows. In this configuration, signals from the two central rows are selected by switching circuitry to produce two thin image slices.

It will be appreciated that by producing two adjoining, thin image slices rather than a single slice of comparable thickness, the dose efficiency of the imaging system is generally enhanced. To maximize this efficiency, the aperture is adjusted so as to generally match a minimum lateral extent of a beam of radiation that is irradiating the object and impinging on the array. This minimum lateral extent is generally determined by the geometry of a radiation source irradiating the object. In this case, the minimum slice thickness is approximately equal to half the lateral extent of the beam of radiation. If only a single slice of this minimum thickness were produced, then only about half of the radiation irradiating the subject would be used in creating the image, so that the dose efficiency would similarly be about 50% less.

Preferably, when the linear aperture is opened to its maximum opening dimension, the switching circuitry combines signals from selected rows of the array to produce four slices having a common thickness, corresponding to the width of outermost rows of the array. Additionally or alternatively, signals from each of the two central rows may be combined with signals from all other, peripheral, rows on its respective side of the array, out to and including the outermost row, so as to produce two slices have a maximum possible thickness.

In one such preferred embodiment of the present invention, the array comprises eight rows of detectors, wherein the two central rows have the smallest width, and the peripheral rows, having greater widths, are symmetrically arranged on both sides of the central rows. The array is coupled to a switching network comprising fourteen switches, which may be of any suitable type known in the art. The array and the switches are coupled to four adders, whose outputs are used to produce two or four image slices of desired thickness, as described above.

In still other preferred embodiments of the present invention, the detector array is mounted on a movable base, which shifts the array laterally, relative to the object being imaged, along an axis perpendicular to the long axes of the rows of the array. In such preferred embodiments, rows of different widths may be arranged asymmetrically relative to a central axis of the array defined by one or more rows of the smallest width, unlike the preceding embodiments, in which the array is generally symmetrical about such an axis. Preferably the movable base is used in conjunction with switching circuitry and a variable aperture, as described above, to produce multiple slices of varying thicknesses, while keeping the slices commonly centered on a central plane, in a fixed relation to the object, regardless of the thickness of slices that is chosen.

The use of the movable base in conjunction with other aspects of the present invention allows an array having a reduced number of rows to be used in producing a desired combination of slice widths. In other words, the use of the movable base allows a greater variety of slice thicknesses to be produced, relative to the number of rows in the detector.

In some preferred embodiments of the present invention, a CT imaging system includes a detector array, as described above, wherein an X-ray tube irradiates the body of a subject, and the detector array is positioned on the opposite side of the body to the tube, so that the detectors receive radiation that has been transmitted through the body. The detector array preferably comprises scintillators and photodiodes or other suitable X-ray detectors known in the art and produces a plurality of sectional image slices, preferably four such slices, although different numbers of slices may similarly be produced. Preferably a collimator is associated with the X-ray tube so as to limit the extent of the X-ray beam irradiating the body to a region of the body containing the slices.

In some of these preferred embodiments, the detector array is planar, i.e., all the detectors are substantially in a single plane. In other preferred embodiments, however, the detector array is arcuate, having a radius of curvature approximately equal to the distance of the array from the X-ray tube, which preferably emits a fan-shaped beam whose angular extent generally corresponds to the angle subtended by the arcuate array. In still other preferred embodiments, in which the CT imaging system preferably comprises a fourth-generation CT scanner, the detector array generally describes a ring, substantially surrounding the body. It will be appreciated that the various arrangements of rows having different widths, as described above, as well as the accompanying switching circuitry, aperture, movable base and other aspects of the present invention, may equally be applied to planar and arcuate detector arrays.

Preferably, the X-ray tube is mounted on a gantry or other suitable apparatus, which revolves about an axis passing through the body. In preferred embodiments of the present invention in which the detector array is planar or arcuate, the array is preferably mounted on the gantry, opposite the X-ray tube, so as to revolve around the body, as is known in the art with regard to third-generation CT scanners. Alternatively, in preferred embodiments of the present invention in which the detector array describes a ring, the array preferably remains rotationally stationary, and only the X-ray tube revolves around the body. In either of these cases, the position of the gantry and detector array translates laterally relative to the body in a direction parallel to the axis, preferably by translational motion of the body relative to the gantry and array. The revolution of the gantry and the translation of the gantry and the detector array relative to the body allow multiple angular views and multiple sectional slices to be acquired.

In alternative preferred embodiments of the present invention, a tiltable, planar detector array comprises a plurality of rows of detectors, all such rows having generally equal widths. The array is coupled to a mechanical tilting device, which controllably tilts the array about a tilt axis substantially parallel to the long axes of the rows. A normal orientation of the tiltable array is defined by a plane that is perpendicular to a line passing through a focal point of the radiation source and perpendicularly intersecting the tilt axis of the array. An effective row width, common to all the rows, is defined by geometrical projection of the lateral dimension of the row onto the plane of the normal orientation. It will thus be understood that as the array tilts away from the normal orientation, the effective widths of the rows decrease, substantially in proportion to the cosine of a tilt angle thereof.

The detectors in each row of the array receive radiation from a corresponding slice of an object being imaged. When the array is substantially in the normal orientation, the detectors have effective widths equal to the full widths of the rows, and thus receive radiation from equal, relatively thick slices of the object. When the array is tilted relative to this direction, however, the effective widths of the detectors are smaller, and therefore, the detectors receive radiation from equal, relatively thinner slices. By tilting the array to various tilt angles, multiple slices having a plurality of different thicknesses are defined.

In still other preferred embodiments of the present invention, a detector array comprises a plurality of rows of detectors having substantially equal widths (and providing substantially equal slice widths), wherein each such row may be controllably tilted about its respective long axis. Preferably all the rows in this preferred embodiment are co-planar and contiguous with their immediate neighbors, when the rows are in a normal orientation, as described in reference to the preceding embodiments. Preferably all rows are tilted to substantially equal angles, so that they define multiple slices having equal, variable thicknesses.

In one such preferred embodiment of the present invention, the rows are moved laterally relative to one another, in a direction perpendicular to their long axes. When the rows are tilted, they are then also moved closer together, so as to maintain substantial contiguity of the thinner slices defined by this tilted orientation.

In still further preferred embodiments of the present invention, a detector array comprises four parallel rows of detectors, including two outer rows and two inner rows, preferably all of equal width, each row corresponding to a respective image slice. The outer rows are adapted to act as a linear aperture with respect to the inner rows, i.e., the outer rows are mounted so that they may be translated laterally to overlap and thus mask portions of the widths of the inner rows. In this way, the thicknesses of the two slices corresponding to the two inner rows are controlled. Preferably, an adjustable aperture or collimator slit masks portions of the widths of the outer rows, so that all four of the outer and inner rows may have any desired effective widths, preferably equal effective widths.

It will be understood that while the above preferred embodiment is described in terms of four rows of detectors, generating four image slices of preferably equal thicknesses, the principle of using one or more rows of the detector array to variably overlap and mask one or more other rows may similarly be applied in other, different preferred embodiments of the present invention, as well. For example, the array may include more than four rows of detectors, so as to produce more than four image slices. The effective widths of these more than four rows of detectors may be controlled by the above principle of overlapping and masking rows, or by other means as described above with reference to other preferred embodiments of the invention.

In yet a further alternative embodiment of the invention a plurality of rows of detectors having equal widths is provided. The outputs of the detectors are summed such that a single wide slice and a single thick slice are produced. Alternatively, one wide slice, flanked by two narrow slices are produced. Further alternatively, a single thin slice flanked by two thin slices are produced. Preferably, these slice widths are produced without masking the detectors. Furthermore, the thicker slices are preferably produced by adding the outputs of a plurality of equal sized detectors while the thinner slices are produced by utilizing the output of a single row of detectors or a sum of a lesser number of detectors than that utilized for producing the thicker slice(s).

In yet another preferred embodiment of the invention, a plurality of rows of different widths is provided, with a thin row or rows at the center and wider rows on one side of or preferably flanking the thin row or rows. In this embodiment of the invention one or more thin slices are provided at the center of the group of rows and thick slices are provided by combining the outputs of detectors of adjoining wider rows. The thin slices may be provided by the detectors of a single row or by combing signals from detectors of adjacent thin rows. In a preferred embodiment of the invention, ratios of 3:1, 5:1, 8:1 or more, such as 10:1 are provided between the thin slices and the thicker slices.

There is therefore provided, din accordance with a preferred embodiment of the present invention, apparatus for producing multiple image slice data responsive to incident radiation passing through an object, including:

a detector array, including a plurality, p, of parallel rows of detector elements, which receive the incident radiation and generate signals in response thereto, each of which rows is characterized by a width, measured in a direction perpendicular to a long dimension thereof; and signal processing circuitry, which receives signals from the detector elements and which combines the signals in a first combination mode to form a set of n groups of rows, each such group of rows having an effective group width substantially equal to the effective group width of each of the other groups, and which further combines the signals in at least m additional combination modes to form different sets of n groups of rows, each such set having a different effective group width common to all groups in the set, wherein p=n+2(m−1).

Preferably, in at least one of the combination modes, at least one of the n groups of rows includes at least one row having a width different from all the rows in at least one other of the n groups of rows.

Preferably, each group of rows includes mutually adjoining rows, and the n groups of rows in each of the combination modes are mutually exclusive.

There is further provided, in accordance with a preferred embodiment of the present invention, apparatus for producing multiple image slice data responsive to incident radiation, including:

a detector array, including a plurality of parallel rows of detector elements, which generate signals responsive to radiation incident thereon, each of which rows is characterized by a width, measured in a direction perpendicular to a long dimension thereof; and signal processing circuitry, coupled to the array, which receives signals from at least four of the rows of the array and produces four or more channels of output data, each such channel including data derived from signals generated by detector elements in one or more rows of the array selected by the circuitry for inclusion of data therefrom in said channel, wherein each row is characterized by an effective row width, defined by a geometrical projection of the portion of the width of the row that is exposed to the radiation, onto a plane that is substantially perpendicular to a direction of propagation of the radiation incident on the array, and wherein each channel of output data is characterized by an effective channel width, defined by the sum of the effective widths of the one or more rows selected by the circuitry for inclusion of data therefrom in the channel, and wherein the effective channel widths of all of the four or more channels are substantially equal, and wherein the number of different effective channel widths that may be selected by the signal processing circuitry is equal to at least half the number of rows in the array, less one.

Preferably, the signal processing circuitry includes switching circuitry, which alternately selects different rows for inclusion of data therefrom in each of the four or more channels, thereby varying the effective channel widths thereof; and two or more adders, each respectively associated with one of the four or more channels, and each of which sums the signals generated by adjacent detectors in two or more respective, adjoining rows of the array that are selected by the circuitry for inclusion of data therefrom in the channel.

Preferably, the array includes two central rows having a common width smaller than or equal to the widths of all the other rows, and the widths of all the rows are substantially equal to integer multiples of the width of the central rows.

Additionally or alternatively, the apparatus includes an adjustable slit or linear aperture, having an aperture that is variable in a direction perpendicular to the long dimension of the rows, which may be variably closed to mask portions of the widths of the rows, thereby varying the effective row widths.

Additionally or alternatively, the apparatus includes a movable base on which the detector array is mounted, which base moves the array in a direction perpendicular to the long dimension of the rows.

Additionally or alternatively, the apparatus includes at least one mechanical tilting device, which controllably tilts a row of the array about a tilt axis substantially parallel to the long dimension of the rows, wherein the effective row width is varied by controlling the at least one tilting device.

There is moreover provided, in accordance with another preferred embodiment of the present invention, apparatus for producing multiple image slice data, responsive to incident radiation, including:

a detector array including at least three detector elements disposed in a lateral direction, which detector elements generate signals responsive to radiation incident thereon, wherein each detector element is characterized by a width, measured in the lateral direction, and wherein at least two of the at least three detector elements have substantially different widths; and circuitry, coupled to the array, which selects a first exclusive group including one or more detector elements and sums the signals generated by the detector elements in the first group to produce a first channel of output data, and which selects a second exclusive group including at least two detector elements and sums the signals generated by the detector elements in the second group to produce a second channel of output data, wherein each detector element is characterized by an effective detector width, defined by the portion of the width of the detector element that is exposed to the radiation, and wherein each channel is characterized by an effective channel width, defined by the sum of the effective detector widths of the one or more detector elements in the group that is selected to produce the channel, and wherein the effective channel widths of the first and second channels are substantially equal.

Preferably, the widths of all of the at least two detector elements having substantially different widths are integer multiples of the width of the one of the at least two detector elements having the smallest width.

There is also provided, in accordance with a preferred embodiment of the present invention, apparatus for producing multiple image slice data responsive to incident radiation, including:

a detector array, including at least a first detector element and a second detector element disposed in a lateral direction, which detector elements generate signals responsive to radiation incident thereon, wherein each detector element is characterized a width in the lateral direction, wherein each detector element is characterized by an effective detector width, defined by the portion of the width of the detector element that is exposed to the radiation, and wherein the second detector element is shifted in the lateral direction relative to the first detector element, so as to overlap and mask a portion of the first detector, thereby altering the first detector's effective width.

Preferably, the apparatus includes an adjustable slit or aperture, which masks a portion of the second detector, thereby altering the second detector's effective width.

There is additionally provided, in accordance with a preferred embodiment of the present invention, apparatus for producing image slice data responsive to incident radiation, including:

a detector array, including one or more rows of detector elements, which generate signals responsive to radiation incident thereon; and at least one mechanical tilting device, which controllably tilts at least one of the one or more rows about a tilt axis thereof, which tilt axis is substantially parallel to the long dimension of the at least one row, wherein the one or more rows are characterized by a width, measured in a direction perpendicular to the tilt axis thereof, and wherein an effective width of the at least one row, defined by a geometrical projection of the width thereof onto a plane that is substantially perpendicular to a direction of propagation of the radiation incident on the row, is varied by controlling the at least one mechanical tilting device.

Preferably, the one or more rows include a plurality of rows, and the mechanical tilting device tilts all of the plurality of rows in the array, more preferably tilting all the rows of the array by a common angle, and most preferably tilting the entire array about a common tilt axis.

Alternatively or additionally, the at least one mechanical tilting device includes a plurality of such devices, which tilt about different, respective axes, wherein each row of the array is preferably tilted about its own respective axis.

Preferably, the apparatus includes a motion control mechanism, which controls a distance between adjoining rows of the array when they are tilted, so that geometrical projections of the rows onto the plane that is substantially perpendicular to the direction of propagation of the radiation incident on the array are substantially contiguous.

There is further provided, in accordance with still another preferred embodiment of the present invention, a CT scanner, for producing images of multiple sectional slices through an object, including:

a radiation source, which irradiates the object from a first side thereof; and apparatus for producing image slice data, as described above, wherein the detector array is positioned on a second side of the object, opposite to the first side.

There is also provided, in accordance with yet another preferred embodiment of the present invention, a detector array switching network, including:

a plurality of detector elements, which generate signals responsive to incident radiation;

a plurality of switches; and two output channels, wherein a first detector element is connected to a first output channel, and wherein a second detector element adjacent to the first detector element, is connected by a first switch to the first output channel and alternatively by a second switch to a second output channel, and wherein a third detector element adjacent to the second detector element, is connected by a third switch to the first output channel and alternatively by a fourth switch to the second output channel, and wherein a fourth detector element adjacent to the third detector element, is connected by a fifth switch to the second output channel, and wherein the switches are controlled so that one of the second, third and fourth detector elements is connected to the second output channel, and other detector elements, if any, between the first detector element and the detector element connected to the second output channel are connected to the first output channel, together with the first detector element.

There is further provided, in accordance with an additional preferred embodiment of the present invention, a detector array switching network, including first and second sub-networks, each such sub-network substantially in accordance with the switching network described above, wherein the respective first detector elements of the first and second sub-networks are mutually adjacent, and wherein the network is substantially symmetrical about a central axis, defined by a border between the respective first detector elements.

There is also provided, in accordance with a preferred embodiment of the present invention, a method for producing multiple-slice images of an object, including:

irradiating the object;

receiving and processing signals generated in response to radiation transmitted through a volume of the object;

dividing the volume into a plurality of substantially contiguous, parallel object slices, each of which slices has a thickness approximately determined by the width of a respective detector that generates signals responsive to radiation transmitted therethrough;

producing four or more substantially contiguous sectional image slices having a common thickness, each such image slice corresponding to one or more adjoining object slices; and reconstructing an image of the volume, said image including at least the four or more sectional image slices, wherein the object slices comprise at least two central slices of substantially equal thickness, which thickness is less than the thickness of each the other object slices, and at least two peripheral slices whose thickness is greater than the thickness of the central slices, and wherein producing four or more image slices having a common thickness comprises producing at least four image slices of thickness substantially equal to the thickness of the two central slices.

There is further provided, in accordance with a preferred embodiment of the invention, a method for producing multiple-slice images of an object, comprising:

irradiating the object;

receiving and processing signals generated in response to radiation transmitted through a volume of the object;

dividing the volume into a plurality of substantially contiguous, parallel object slices, each of which slices has a thickness approximately determined by the width of a respective detector that generates signals responsive to radiation transmitted therethrough;

producing two or more substantially contiguous sectional image slices having at least two different thicknesses, each such image slice corresponding to one or more adjoining object slices; and reconstructing an image of the volume, said image including at least the two or more sectional image slices, wherein the thickness of the widest reconstructed slice and the thickness of the thinnest image slice have a ratio of at least 3:1, In preferred embodiments of the invention the ratio is at least 5:1 or 8:1. In a preferred embodiment of the invention, the ratio is about 10:1.

There is further provided, in accordance with a preferred embodiment of the invention, a method for producing multiple-slice images of an object, comprising:

irradiating the object;

receiving and processing signals generated in response to radiation transmitted through a volume of the object;

dividing the volume into a plurality of substantially contiguous, parallel object slices of equal width, each of which slices has a thickness approximately determined by the width of a respective detector that generates signals responsive to radiation transmitted therethrough;

producing two or more substantially contiguous sectional image slices having at least two different thicknesses, each such image slice corresponding to one or more adjoining object slices; and reconstructing an image of the volume, said image including at least the two or more sectional image slices.

There is further provide, in accordance with a preferred embodiment of the invention a method for producing multiple-slice images of an object, comprising:

irradiating the object;

receiving and processing signals generated in response to radiation transmitted through a volume of the object;

dividing the volume into a plurality of substantially contiguous, parallel object slices, each of which slices has a thickness approximately determined by the width of a respective detector that generates signals responsive to radiation transmitted therethrough;

producing two or more substantially contiguous sectional image slices having at least two different thicknesses, at least one such image slice corresponding to a plurality of adjoining object slices; and reconstructing an image of the volume, said image including at least the two or more sectional image slices.

In a preferred embodiment of the invention, the object slices are of substantially the same thickness.

In various preferred embodiments of the invention, the image slices comprise a single thin slice and a single thick slice or a single thin slice and two thick slices or a single thick slice and two thin slices.

BRIEF DESCRIPTION OF THE DRAWINGS

The present invention will be more fully understood from the following detailed description of the preferred embodiments thereof, taken together with the drawings in which:

FIGS. 5A–5D are sectional representation of a detector array and a mechanical aperture associated therewith, in accordance with a preferred embodiment of the present invention;

FIGS. 6A–6D are sectional representations of a detector array, together with an associated mechanical aperture and movable base, in accordance with a preferred embodiment of the present invention;

FIGS. 9A–9E are sectional representations of a detector array and a mechanical aperture associated therewith, in accordance with a preferred embodiment of the present invention;

DETAILED DESCRIPTION OF PREFERRED EMBODIMENTS

Figure 1:
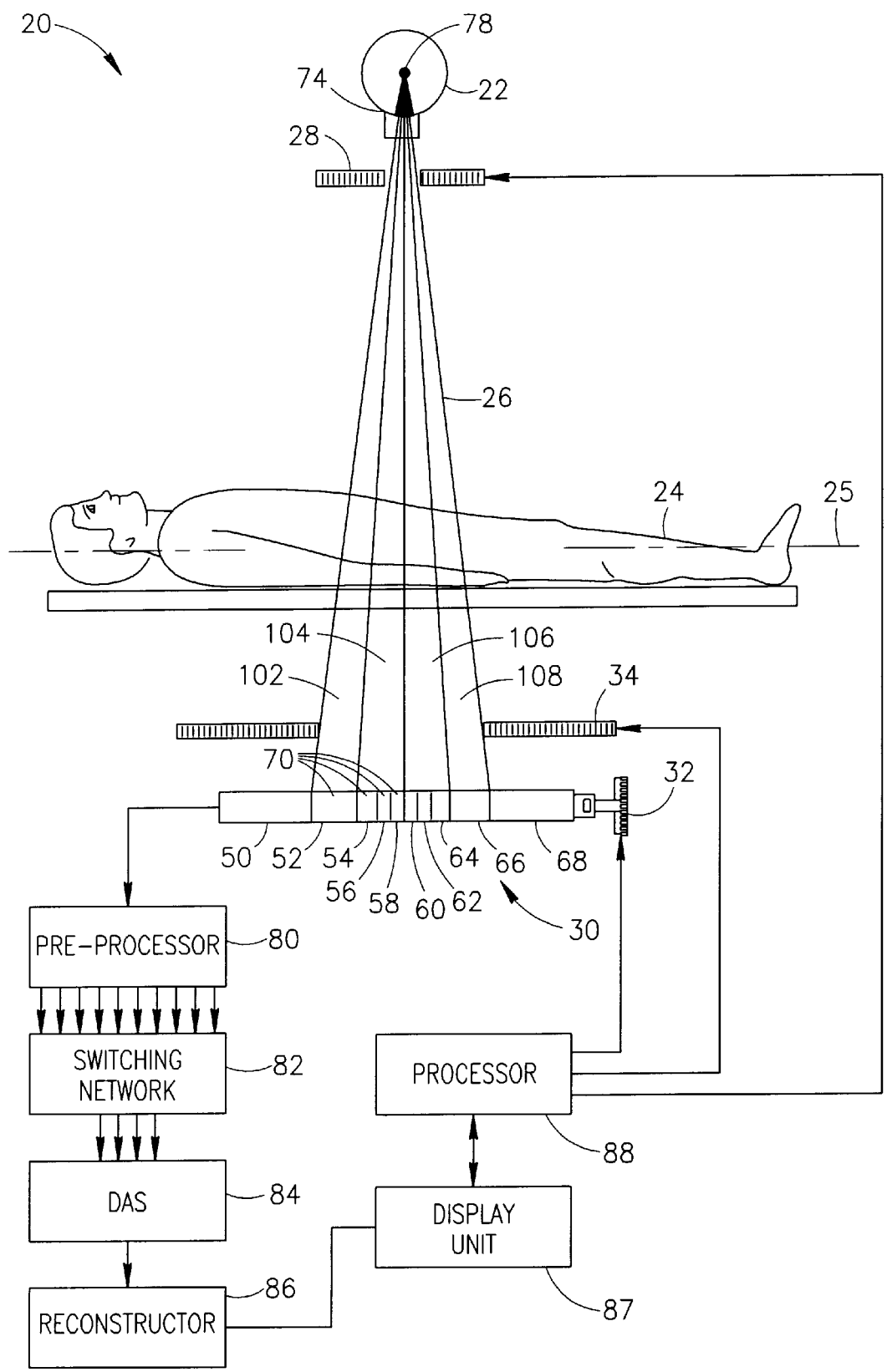
FIG. 1 is a schematic, partly sectional representation of a CT scanner, in accordance with a preferred embodiment of the present invention.

FIG. 1 shows a schematic side view of a CT scanner 20 in accordance with a preferred embodiment of the present invention. An X-ray tube 22 irradiates a region of the body 24 of a subject being imaged. The angular extent of a beam of radiation 26 is preferably restricted by an adjustable collimator 28. X-rays transmitted through body 24 are received by a multi-slice detector array 30, as will be described below. The lateral dimension of array 30, i.e., the dimension parallel to long axis 25 of body 24, is exaggerated in FIG. 1 for the purpose of clarity in the explanation that follows below. Array 30 may be mounted as shown to a movable base 32, which moves and aligns the array relative to an axis defined by X-ray tube 22. In some preferred embodiments of the present invention, collimator 28 and/or a mechanical aperture 34 limits the angular extent of the radiation beam striking array 30. Preferably, collimator 28 is adjusted so as to limit the angular extent of beam 26 to the region of body 24 being imaged by array 30, and minimize irradiation of other regions of the body. Base 32 and/or aperture 34 are particularly useful in conjunction with certain preferred embodiments of the present invention, such as those shown in FIGS. 5A–5D, 6A–6D and 9A–9E and described hereinbelow. The base and the aperture are not essential to the operation of array 30, but are shown in FIG. 1 by way of illustration.

Figure 2:
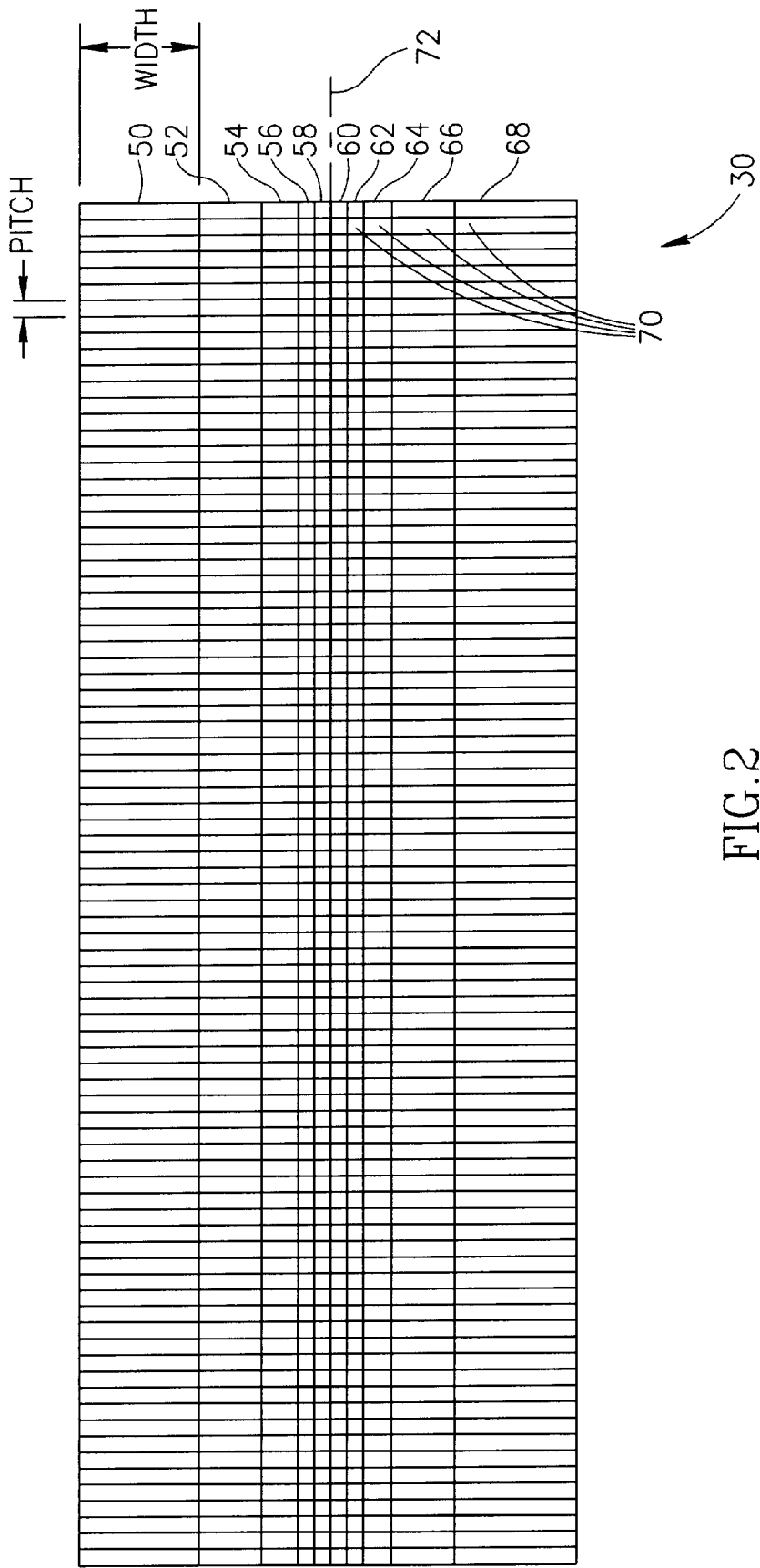
FIG. 2 is a schematic representation of a detector array, in accordance with a preferred embodiment of the present invention.

Reference is now made additionally to FIG. 2, which is a schematic view of array 30, viewed from above in the perspective of FIG. 1. As shown in FIG. 2, array 30 comprises a plurality of rows 50, 52, 54, 56, 58, 60, 62, 64, 66 and 68, each such row comprising a plurality of detector elements 70. Detector elements 70 may comprise any suitable type of radiation-sensitive detectors, for example photodiodes or other detectors known in the art. Preferably, multiple elements 70 are fabricated and/or mounted together on a common substrate, although alternatively elements 70 may be discrete elements, without a common substrate.

Along a direction parallel to the long axis 72 of array 30, detector elements 70 preferably all have a substantially equal dimension, or pitch, as shown in FIG. 2. In the direction perpendicular to axis 72, however, some of the rows have different widths. Central rows 58 and 60 have the smallest width, while peripheral rows have widths equal to or greater than this smallest width, and exterior rows 50 and 68 have the greatest widths. In the preferred embodiment of the present invention shown in FIG. 2, all rows have widths that are integral multiples of the width of the central rows, wherein if the width of rows 58 and 60 is taken to be equal to 1, the remaining rows have the following widths:

Rows 56, 62—width=1
Rows 65, 64—width=2
Rows 52, 66—width=4
Rows 50, 68—width=8

The reasons for this choice of proportions will be explained below.

Figure 3A:
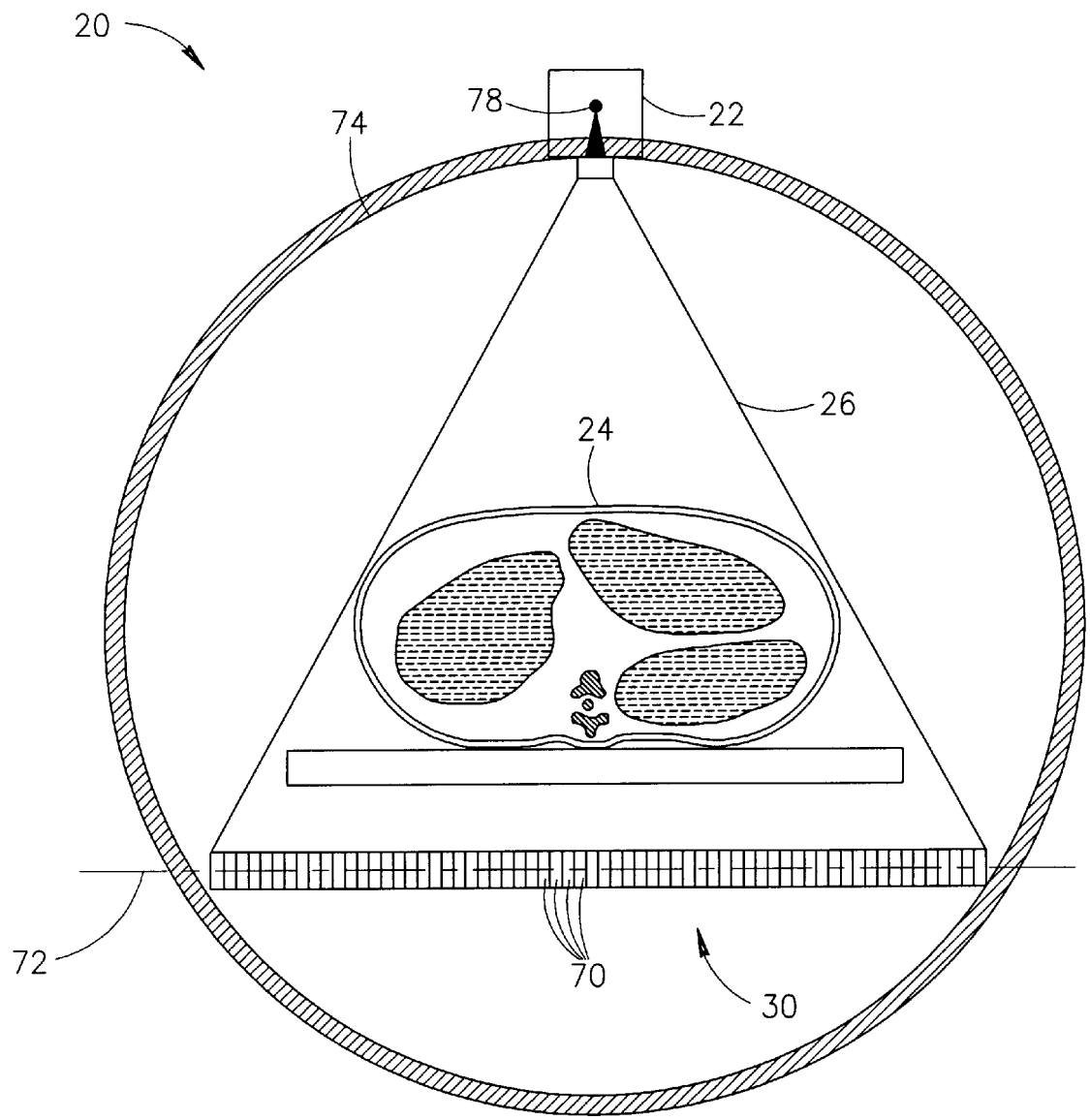
FIG. 3A is a cross-sectional view of the CT scanner shown in FIG. 1.

FIG. 3A is a cross-sectional view of the scanner shown in FIG. 1. Array 30 is mounted in CT scanner 20 with its long dimension, indicated by axis 72, transverse to long axis 25 (shown in FIG. 1, and perpendicular to the plane of FIGS. 3A and 3B) of body 24. Each element 70 of array 30 receives radiation that has traversed body 24 along a linear path from a focal point 78 of X-ray tube 22 to the element, and generates an electrical signal indicative of the attenuation of tissue in the body intercepted by this path. Array 30 and X-ray tube 22, along with ancillary apparatus, such as collimator 28, are mounted on gantry 74. The gantry revolves around an axis substantially parallel to axis 25, so that array 30 can capture views from different angles with respect to this axis. Body 24 is further translated laterally relative to gantry 74, in a direction substantially parallel to axis 25, so that different cross-sectional portions of body 24 may be imaged.

Figure 3B:
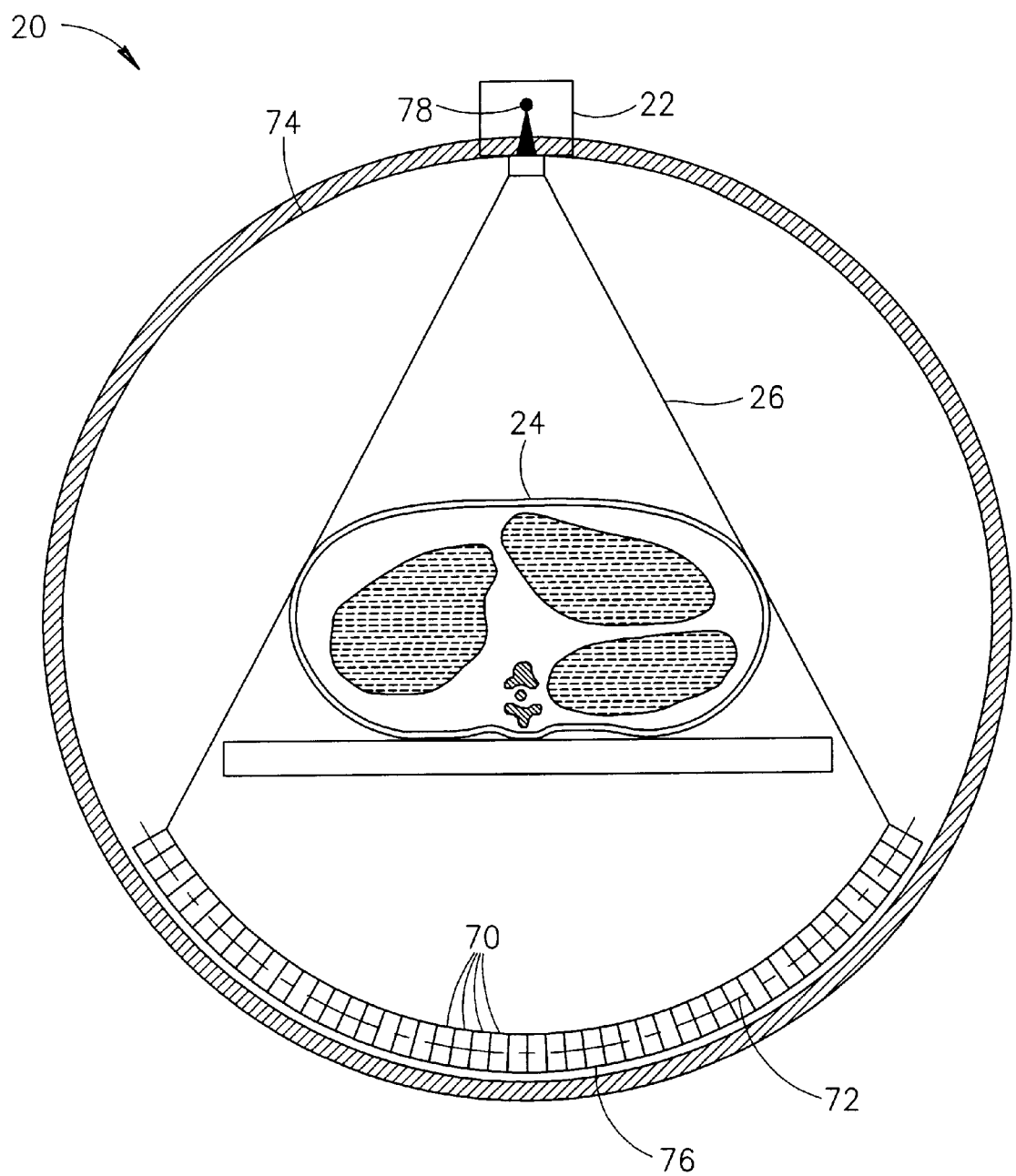
FIG. 3B is a cross-sectional view of a CT scanner similar to that shown in FIG. 3A, but including a detector array in accordance with an alternative preferred embodiment of the present invention.

FIG. 3B shows an alternative preferred embodiment of the present invention, wherein array 76 is arcuate, rather than planar. The arrangement of rows and detector elements in array 76, however, is identical to that of array 30, and in all other respects, the preferred embodiment shown in FIG. 3B is substantially identical to that shown in FIGS. 1, 2 and 3A. The radius of curvature of array 76 is generally equal to the distance from the array to focal point 78. Thus, all elements 70 in array 76 subtend substantially equal angles of beam 26 in the transverse direction. As is known in the art, this equality of angles is useful in reducing angular distortion in the image of body 24 that is produced by CT scanner 20. Although the following preferred embodiments of the present invention will be described with reference to planar detectors arrays, it will be appreciated that arcuate arrays may similarly be used in such embodiments.

Figure 3C:
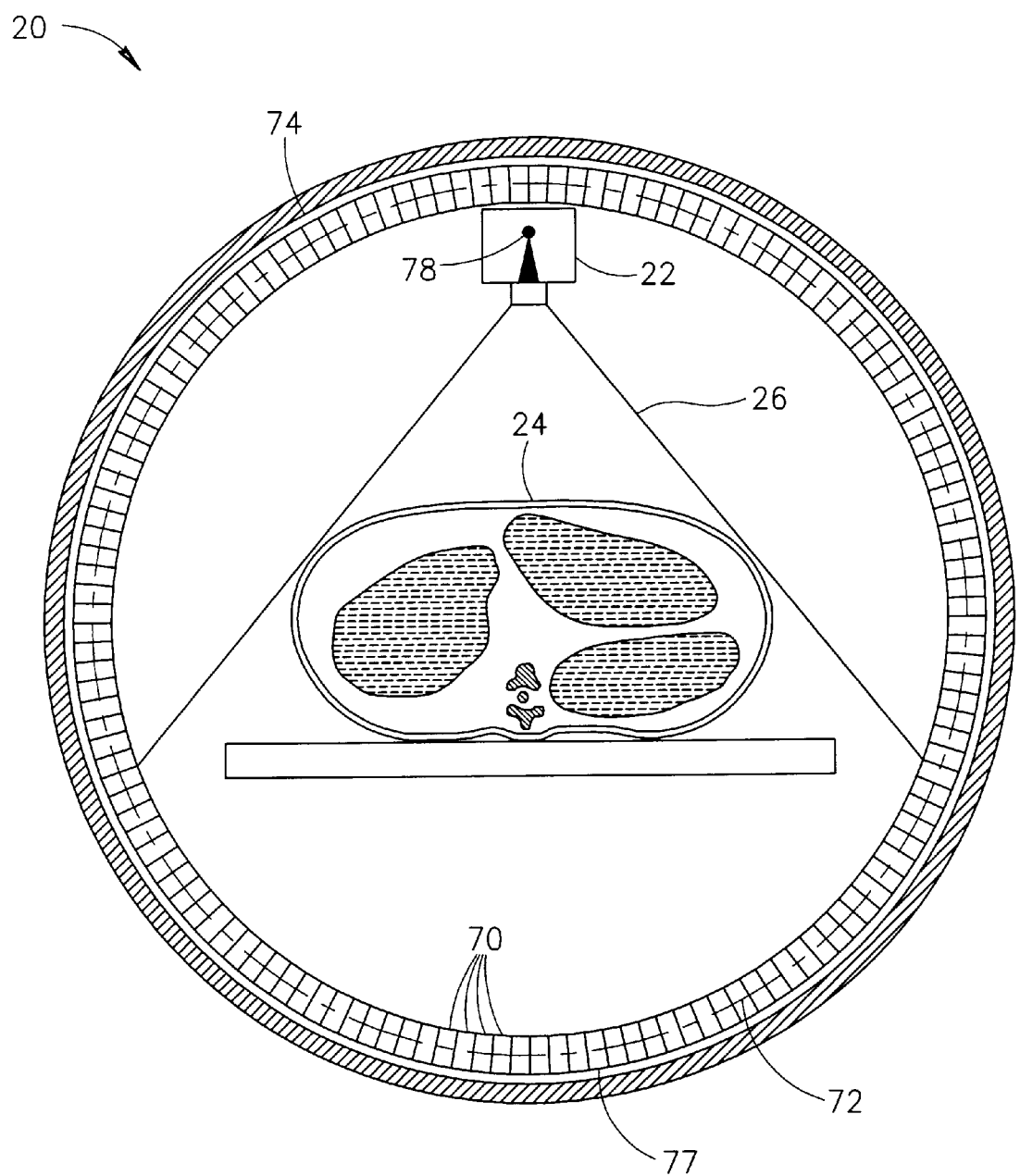
FIG. 3C is a cross-sectional view of a CT scanner in accordance with still another preferred embodiment of the present invention.

FIG. 3C shows still another, alternative, preferred embodiment of the present invention, wherein array 77 describes a ring shape, substantially surrounding body 24. In this preferred embodiment, scanner 20 is preferably a fourth-generation CT scanner. As in the embodiment of FIG. 3B, the arrangement of the rows and detector elements 70 in array 77 is substantially identical to that of array 30. In other respects, array 77 is used in system 20 in a manner substantially similar to that shown in FIGS. 1 and 2 and described herein, except that whereas arrays 30 and 76 preferably revolve around body 24 on gantry 74, array 77 is preferably substantially stationary.

Referring again to FIG. 1, the signals generated by elements 70 are processed by pre-processing circuitry 80 and then transferred via a switching network 82 to a data acquisition system (DAS) 84. A reconstructor 86 receives data from DAS 84 and applies algorithms, as are known in the art, to reconstruct images showing internal structures within body 24. These images are preferably displayed by a display unit 87. A processor 88 receives these images and, optionally, records them in mass memory, prints them on hard-copy media and performs other data and display processing functions known in the art. Processor 88 preferably includes a computer, which controls other components of CT scanner 20, including collimator 28, aperture 34, movable base 32 and gantry 74.

Pre-processing circuitry 80 may be of any type known in the art, and may be integrated on a common substrate with array 30, or contained on a separate substrate or circuit board. Preferably the pre-processing circuitry includes analog pre-amplifiers.

Switching network 82 preferably selects the rows of array 30 from which data are to be acquired, and adds together signals generated by elements in selected, adjacent rows. The switching network may be integrated with array 30 on a common substrate or contained on a separate substrate or circuit board.

Although in the preferred embodiment shown in FIG. 1, switching network 82 receives signals from array 30 after processing by pre-processing circuitry 80, in other preferred embodiments of the present invention, the switching network may select and add together signals from adjacent rows before the signals are pre-processed. Such embodiments may generally be advantageous in reducing the number of components in the system, and thus reducing the system's cost, particularly if switching network 82 is integrated on a common substrate with array 30. Switching of signals before pre-processing however, may also tend to introduce a greater degree of noise into the signals.

In still other preferred embodiments of the present invention, switching network 82 may be eliminated, and instead signals from all the rows of array 30 may be acquired separately by DAS 84, and then signals from adjacent rows may be selected and added together by software processing.

DAS 84 preferably digitizes signals received from switching network 82, using analog-to-digital (A/D) conversion circuitry known in the art. Preferably a logarithm operation is then performed on the digitized signals, for example using look-up tables.

The foregoing order of operations, wherein signals generated by elements 70 are first summed, then digitized and then undergo a logarithm operation, is advantageous in that it reduces the number of electronic components required in the system, and thus reduces the cost of the system, as well. In other preferred embodiments of the present invention, however, the order of these operations may be different.

For example, in one such preferred embodiment, pre-processing circuitry 80 also includes a logarithmic amplifier for each active detector, which results in reduced partial volume artifacts, as is known in the art. Switching network 82 then serializes, selects and adds together signals, and network 82 digitizes the signals, as described above.

In other preferred embodiments of the present invention, pre-processing circuitry 80 may include analog-to-digital (A/D) conversion circuitry. Switching network 82 includes digital circuitry, as is known in the art, which serializes, selects and sums the signals. A logarithm operation may be performed by logarithmic amplifiers included in pre-processing circuitry 80, as described above, or alternatively may be performed digitally, for example by look-up table. Such preferred embodiments will tend to be costly to produce, since they must generally include multiple A/D conversion circuits, but they will generally have the advantage of improved signal/noise ratio.

As illustrated by FIG. 1, by way of example, the rows and/or combinations of rows selected by switching network 82 define substantially parallel image slices 102, 104, 106 and 108 within the angular extent of X-ray beam 26. Slice 102 is reconstructed, by reconstructor 86, using data derived from row 52; slice 104 is reconstructed using data from rows 54, 56 and 58; slice 106 from rows 60, 62 and 64; and slice 108 from row 66. Data from rows 50 and 68 are not used in this case. Preferably collimator 28 and aperture 34 are adjusted so as to limit the angular extent of beam 26 to angle subtended by slices 102, 104, 106 and 108, so as to reduce unwanted radiation dosage, but this adjustment is not necessary to the operation of the preferred embodiment shown here, as long as radiation traversing body 24 can reach all the rows selected by the switching network.

It will be understood that the thickness of each of the image slices, i.e., its lateral dimension measured along axis 25, is generally determined approximately by the width of the row or the sum of the widths of the multiple rows defining the slice. Thus, thinner or thicker slices may be produced by appropriate selection of the rows of the array. Preferably all four slices 102, 104, 106 and 108 are of substantially equal thicknesses.

The actual slice thicknesses are determined only approximately by the row widths, because the thicknesses also depend on optical qualities of other elements of scanner 20, such as X-ray tube 22 and collimator 28. Generally, however, these other elements have only minor effect on the slice thicknesses, as will be illustrated by the following example:

Assuming focal point 78 of X-ray tube 22 to have a dimension f, and rows 56 and 62, the narrowest rows of array 30, to have width w, the effective thickness $a_{eff}$ of an image slice defined by row 56 or 62 will typically be given (neglecting the generally insignificant effect of collimator 28) by:

$$a_{eff}=1/M*SQRT[w^2+(M-1)^2f^2]$$

where $a_{eff}$ is measured at the center of rotation of gantry 74, and M, the magnification, is the ratio of the distance from focal point 78 to array 30, over the distance from the focal point to the center of rotation. Taking typical values of w=2 mm, f=1 mm and M=2, we find that $a_{eff}$=1.1 mm, rather than 1 mm, which would be the slice thickness if focal point 78 were infinitesimal. It will be appreciated that when wider rows of the array are used, the effect of the other elements of scanner 20 on the slice thickness will be even less significant.

As noted earlier, it will be understood that the use of the term "substantially" or "approximately" in stating a detector width dimension, for example to say that the width of rows of detectors are substantially equal, or that the thickness of one row is substantially an integer multiple of another row, means that the detector thickness is such that the slices traversed by the radiation beam has approximately the stated dimension or ratio. This includes any correction to the detector width which might be required, for example to correct for the difference between the effective thickness $a_{eff}$ and the thickness that would be obtained if focal point 78 were infinitesimal or for other geometrically caused variation between the effective slice width and the detector width. Such correction is generally very small compared to the detector and slice dimensions of interest.

The size of focal point 78, together with other geometrical factors, such as the position of collimator 28 and the size of its aperture, also determines a minimum extent of beam 26 at the center of rotation, as is known in the art. In typical CT system geometries, such as that shown in FIG. 1, this minimum extent is significantly larger than the dimension f of the focal point. Thus, if only a single slice of a minimum thickness, for example 1 mm, is acquired by scanner 20, substantial radiation will pass through body 24 outside the bounds of this single slice. The system in this case will have a relatively low dose efficiency. On the other hand, when multiple slices are acquired simultaneously, as described herein, more or substantially all of the radiation incident on body 24 is captured by detector array 30 and used in creating the CT image, so that dose efficiency is increased.

FIGS. 4A-4D schematically illustrate the row-adding function of switching network 82 with respect to array 30, which is shown in cross-section in the figure. In these figures, switching network 82 includes two adders 90 and 92 and four output channels, 94, 96, 98 and 100, corresponding to four image slices, labeled slice A though slice D, respectively. Adders 90 and 92 may be of any suitable type known in the art, for example multi-input analog operational amplifiers or digital adder circuits (in the case that the signals received by network 82 have first been digitized). Pre-processing circuitry 80 is omitted in these figures, for simplicity of illustration (and, as described above, because pre-processing may be performed after switching). As described above, switching network 82 may receive the signals from elements 70 before they are pre-processed.

Figure 4A:
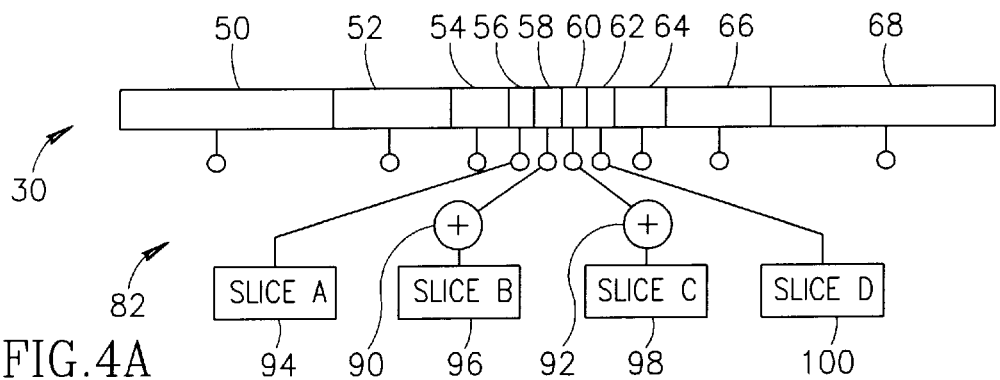
FIGS. 4A–4D are sectional representations of the detector array of FIG. 2, together with schematic representation of switching circuitry associated therewith, in accordance with a preferred embodiment of the present invention.

In FIG. 4A, channels 94, 96, 98 and 100 receive signal data from rows 56, 58, 60 and 62, respectively. In this case, image slices A through D have the smallest possible thickness, corresponding to detector row width=1, where the width of rows 58 and 60 ( as well as 56 and 62) has been taken to be equal to 1, as described earlier. In this case, CT scanner 20 will produce images having the highest available resolution in the lateral direction, although possibly at the expense of lower volume coverage for a given scanning duration and/or reduced signal/noise ratio.

Figure 4B:
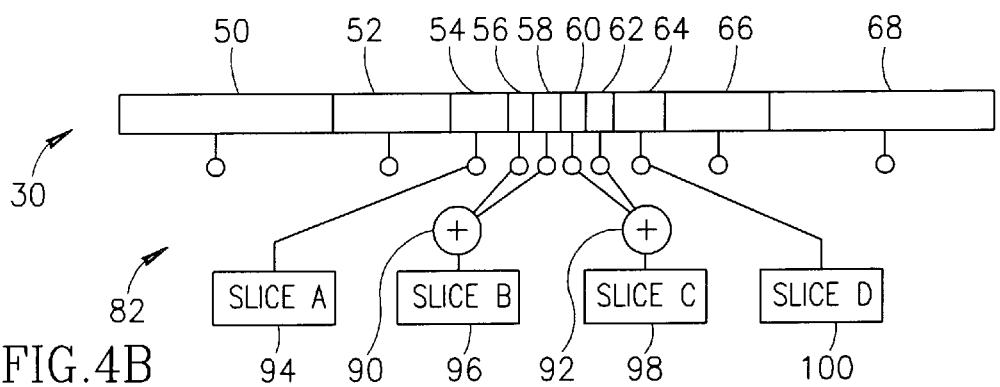

In FIG. 4B, channels 94 and 100 receive signal data from rows 54 and 64, which have width=2. Channel 96 receives data derived by summing signals using adder 90, wherein the signal from each element in row 56 is summed with that from an adjacent element in row 58, so that channel 96 corresponds to an effective row width=2, i.e., the sum of the widths of rows 56 and 58; and channel 98 similarly receives data summer by adder 92 from rows 60 and 62. In this case, slices A through D have a common thickness that is approximately twice that of the slices produced in the configuration shown in FIG. 4A.

Figure 4C:
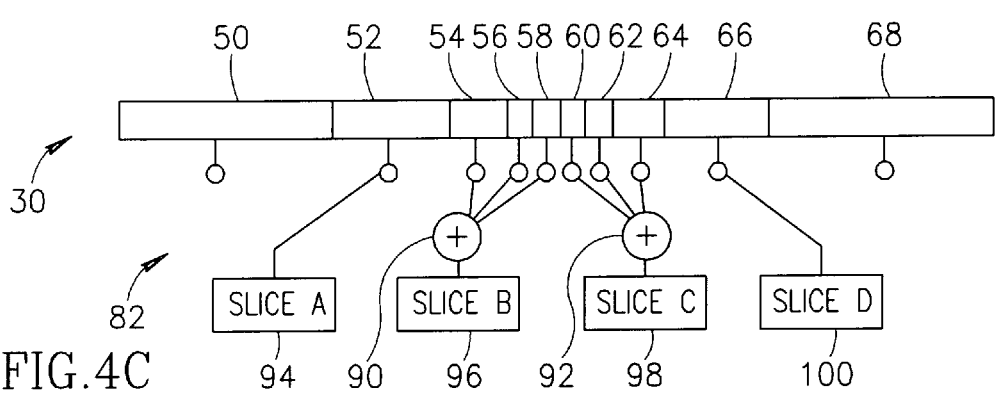

FIG. 4C shows still another configuration, in which each of channels 94, 96, 98 and 100 receives data corresponding to an actual or effective row width=4, producing image slices as illustrated by slices 102, 104, 106 and 108 in FIG. 1.

Figure 4D:
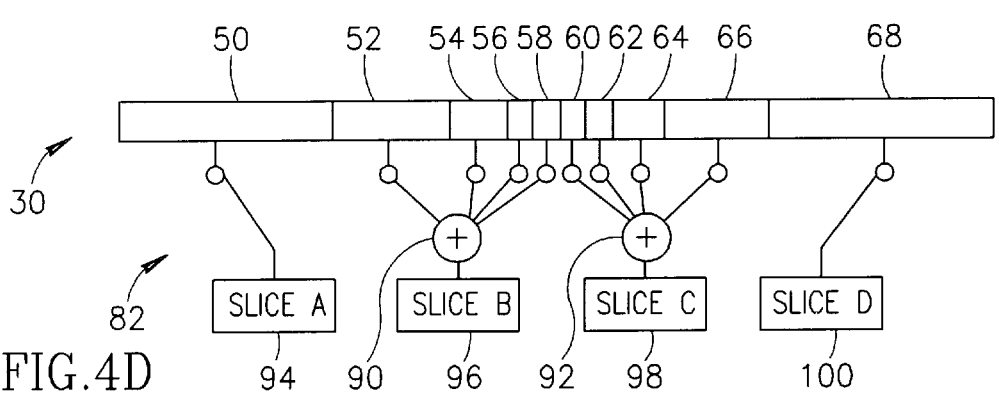

FIG. 4D shows another configuration, in which all the rows of array 30 are used to produce slices having a maximal thickness, approximately eight times as thick as the slices defined by the configuration of FIG. 4A. The configuration of FIG. 4D will generally enable CT scanner 20 to operate at its highest throughput rate and highest signal/noise ratio.

It will be appreciated that detector array 30 as illustrated by FIG. 2, operating in accordance with FIGS. 1, 3A and 4A–4D, enables CT scanner 20 to acquire four image slices, of equal thickness, simultaneously. The slice thicknesses may be varied electronically, without the use of moving parts, over a range of approximately 1:8. Array 30, however, includes only ten rows of detector elements 70, so that the complexity and cost of pre-processing circuitry 80 and switching network 82 may be reduced relative to comparable circuitry that must be used for producing multiple slices of similarly variable thicknesses in conjunction with other detector arrays known in the art.

It will further be appreciated that although the preceding preferred embodiment, as well as other preferred embodiments of the present invention described below, is shown to produce four image slices with four alternative choices of slice thickness, the principles of the present invention may similarly be applied to produce a greater number of slices and a greater or smaller range of thicknesses. The number of slices and the thicknesses thereof, in such embodiments of the present invention, are generally dependent on the number of rows in the detector array and the construction and function of a switching network associated therewith.

FIGS. 5A–5D illustrate an alternative preferred embodiment of the present invention, wherein a detector array 100 has structure and function generally similar to those of array 30, but the rows of array 100 have different relative widths, specifically:

Central rows 112, 114—width=1
Rows 110, 116—width=2
Rows 108, 118—width=4
Rows 106, 120—width=3
Rows 104, 122—width=10.

Figure 5C:
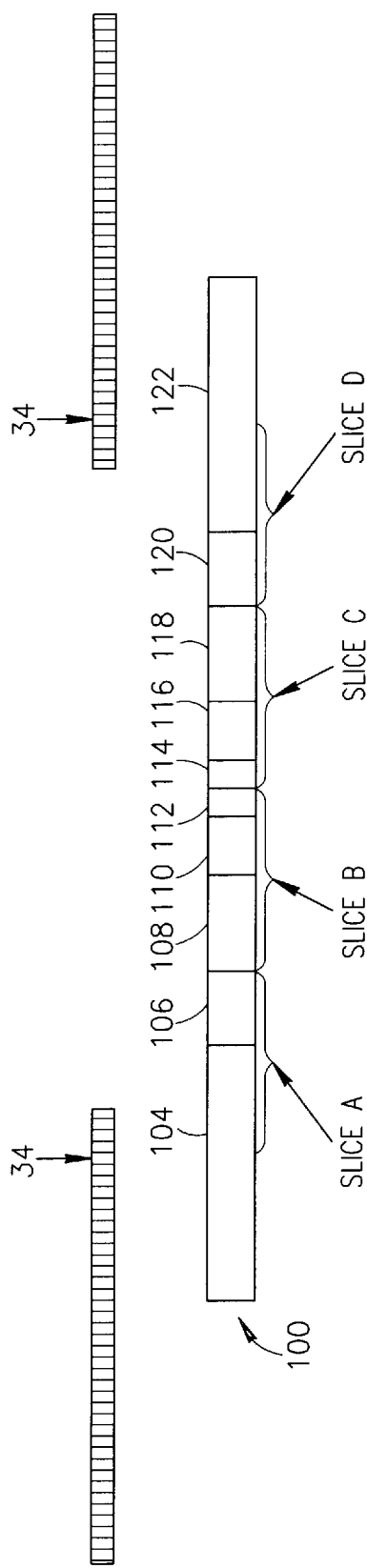

In the preferred embodiment shown in FIGS. 5A–5D, mechanical aperture 34 is controlled to selectively mask some of the rows in array 100. Preferably, collimator 28 is also adjusted so as to limit the angular extent of beam 26 to the extent of aperture 34 shown in the figures. Collimator 28 may, alternatively, be used instead of aperture 34 for this purpose. As shown in FIGS. 5A–5C, this selective masking may include limiting the effective widths of some of the rows. Switching circuitry similar to network 82, as illustrated in FIGS. 4A–4D, selects and adds together signals from adjacent rows of array 100, so as to produce four slices labeled slice A, B, C and D, as above.

Thus, in FIG. 5A, aperture 34 is narrowed laterally so as to mask substantially one half of the widths of rows 110 and 116, and the effective widths of these rows are then substantially equal to 1, like rows 112 and 114. In this case, four relatively thin slices A–D are produced, corresponding to row width=1.

In FIG. 5B, aperture 34 is opened so that rows 10 and 116 are fully exposed, and substantially one fourth of the widths of rows 108 and 118 are masked, so that these rows have effective width=3. Signals from rows 110 and 112 are combined in slice B, thus producing a similar effective width=3, and likewise rows 114 and 116 in slice C.

In FIG. 5C, aperture 34 is opened still further, so as to mask substantially 60% of the widths of rows 104 and 122, and expose all other rows fully. In this case, the four slices have thickness corresponding to effective row width=7.

Figure 5D:
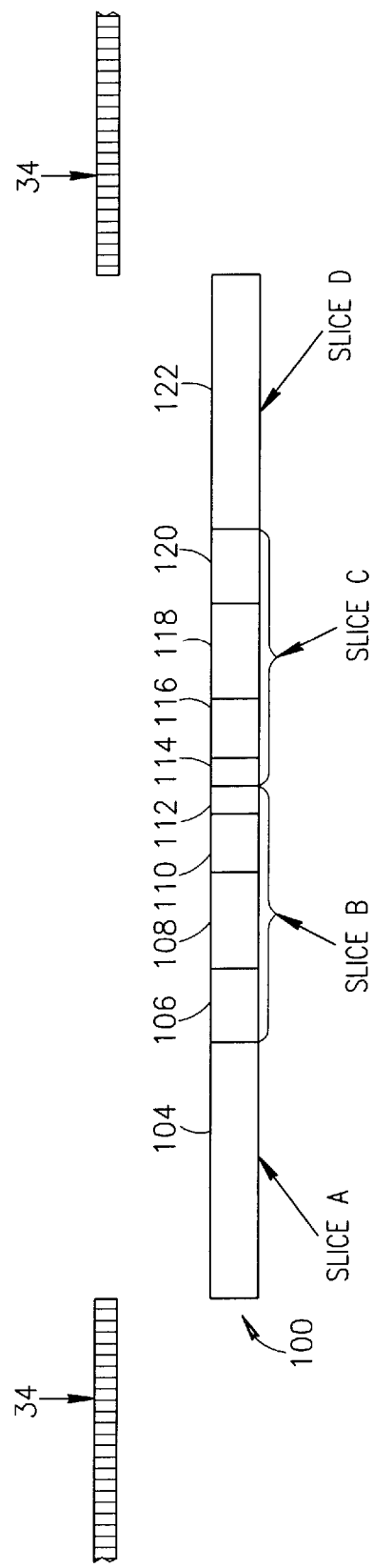

Finally, in FIG. 5D, aperture 34 is fully open, and the four slices have thickness corresponding to effective row width=10.

It will be appreciated that preferred embodiments of the present invention that make use of a variable aperture, such as collimator 28 or mechanical aperture 34, in the manner described here can typically generate a wider range of choices of slice thicknesses than can embodiments that use electronic switching alone, such as that shown in FIGS. 4A–4D.

FIGS. 6A–6D illustrate an alternative preferred embodiment of the present invention, using a detector array 130, which has structure and function generally similar to those of arrays 30 and 122, but having rows of different relative widths, which vary asymmetrically about a central axis of the array parallel to the rows. Specifically:

Rows 138, 140—width=1
Row 136—width=2
Row 134—width=4
Rows 132, 142, 144—width=8.

In the preferred embodiment shown in FIGS. 6A–6D, as in the preceding embodiment, mechanical aperture 34 is controlled to mask some of the rows in array 130, so as to limit their effective widths. Movable base 32 further controls the lateral position of array 130, relative to an axis 146 perpendicular to the surface of the array and passing through focal point 78. Switching circuitry similar to that illustrated in FIGS. 4A–4D selects and adds together signals from adjacent rows of array 130, so as to produce four slices labeled slice A, B, C and D, as above.

In FIG. 6A, mechanical aperture 34 masks portions of rows 136 and 142, so that these two rows have effective width=1, and four image slices are produced having a minimum thickness corresponding to this width.

In FIG. 6B, movable base 32 shifts the position of array 130, so that a common edge of adjoining rows 136 and 138 is substantially aligned with axis 146. Mechanical aperture 34 opens asymmetrically, so as to mask portions of rows 134 and 142. Four image slices corresponding to effective row width=2 are thus produced.

Figure 6C:
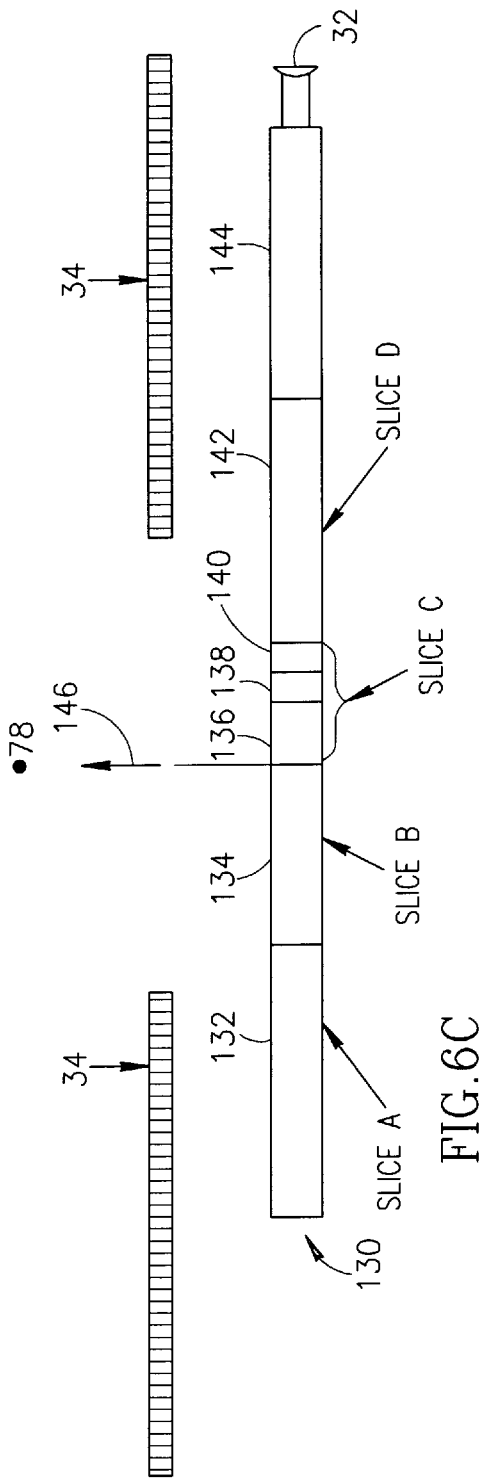

In FIG. 6C, movable base 32 shifts array 130 still further, so that a common edge of adjoining rows 134 and 136 is substantially aligned with axis 146, and aperture 34 opens so as to mask portions of rows 132 and 142. Four image slices are produced corresponding to effective row width=4.

Figure 6D:
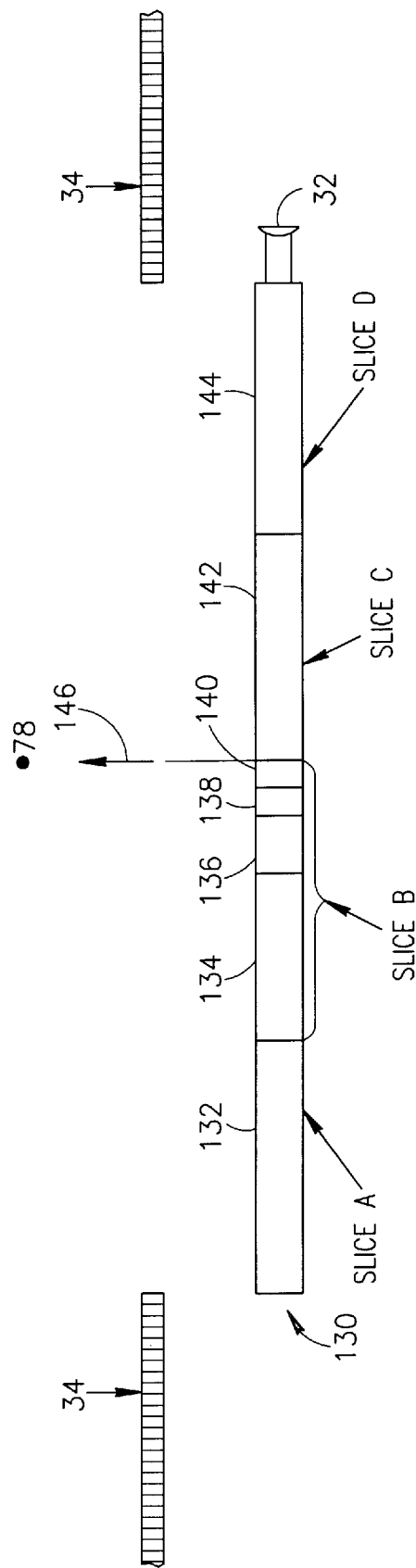

In FIG. 6D, aperture 34 is fully opened, and movable base 32 shifts array 130 back to align a common edge of adjoining rows 140 and 142 with axis 146. Four image slices are produced corresponding to effective row width=8.

It will be appreciated that array 130, as shown in FIGS. 6A–6D, achieves the same range and values of slice thicknesses as does array 30, as illustrated by FIGS. 4A–4D; but array 130 includes only seven rows of detector elements, while array 30 has ten rows. Thus, array 130 can achieve resolution that is comparable to that of array 30, but with substantially fewer detector elements in the array, and a correspondingly simpler switching network.

Figure 7A:
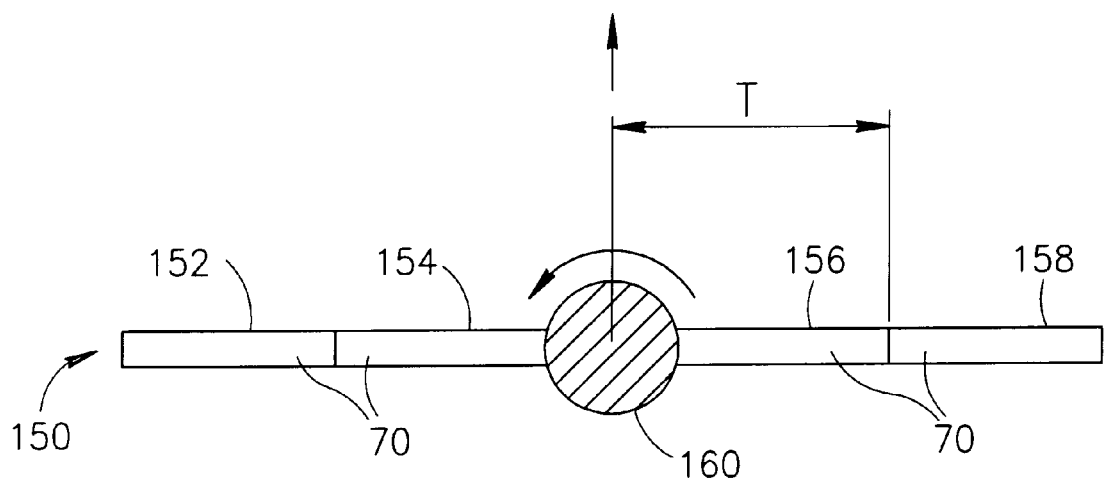
FIGS. 7A–7B are sectional representations of a tiltable detector array, in accordance with a preferred embodiment of the present invention.
Figure 7B:
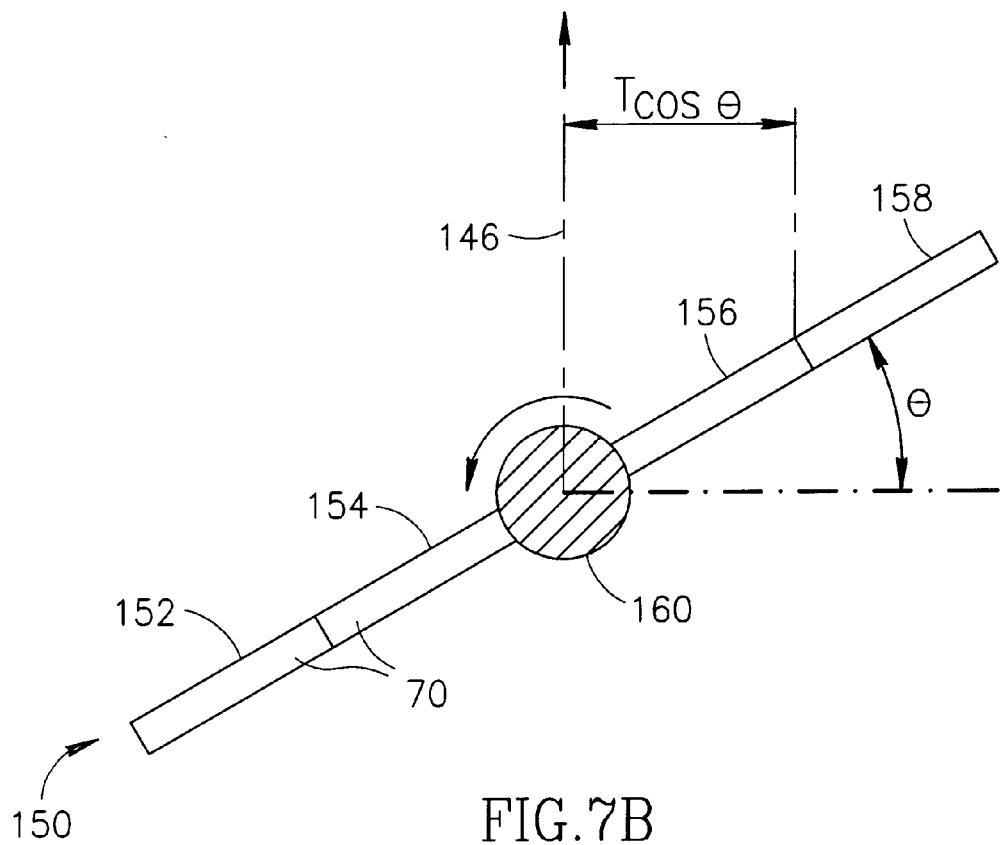

FIGS. 7A and 7B show an alternative preferred embodiment of the present invention, in which a planar detector array 150 comprises a plurality of detectors 70 arranged in four rows 152, 154, 156 and 158 of equal widths. Array 150 may be used in CT scanner 20 in place of detector array 30 shown in FIG. 1. Array 150 is mounted on a pivot 160, which rotates about an axis parallel to the long axes of the rows, preferably under the control of processor circuitry, such as processor 88. The array is coupled to pre-processing, DAS and reconstructor circuitry similar to that illustrated in FIG. 1, but switching network 82 may be eliminated.

As shown in FIG. 7A, when array 150 is oriented so that the plane of the array is substantially perpendicular to axis 146 (as described in reference to FIGS. 6A–6D), CT scanner 20 will produce four image slices having a common thickness T, determined by the width of the rows. As FIG. 7B shows, however, when array 150 is tilted, due to rotation of pivot 160, the thickness of the slices is reduced to a value approximately equal to Tcosθ, where θ is the angle of rotation of the array relative to its starting position. By rotating array 150 through an angle θ=82.8°, the slice thickness may be reduced to approximately T/8. Provision must be made, for example in reconstructor 86, for small differences that will arise in the relative strengths of the signals among the four rows and in the corresponding slice thicknesses, due to rows 156 and 158 being closer to focal point 78 than rows 154 and 152.

Figure 8A:
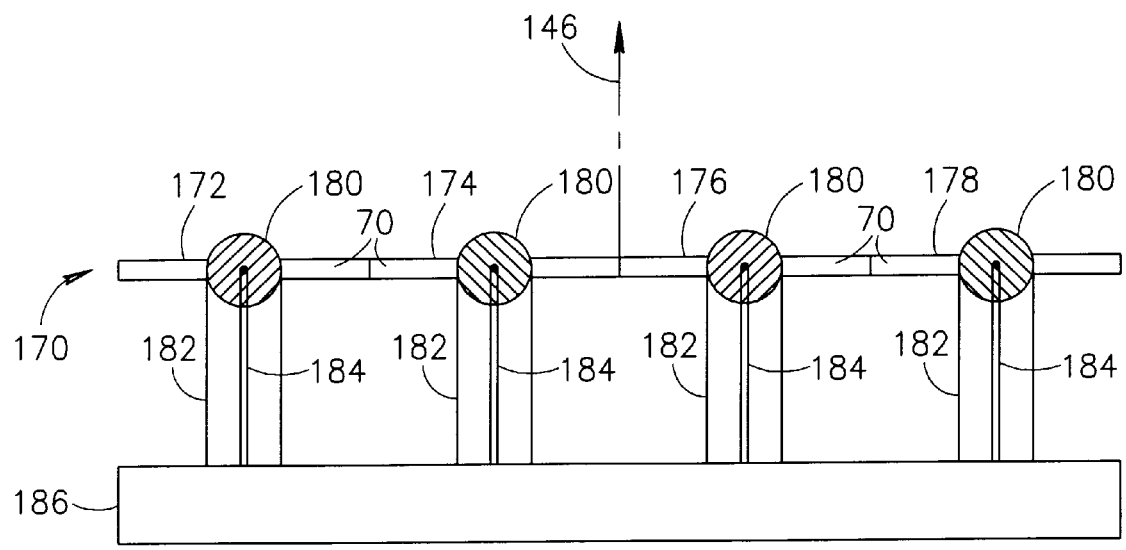
FIGS. 8A–8B are sectional representations of an array of tiltable rows of detectors, in accordance with another preferred embodiment of the present invention.
Figure 8B:
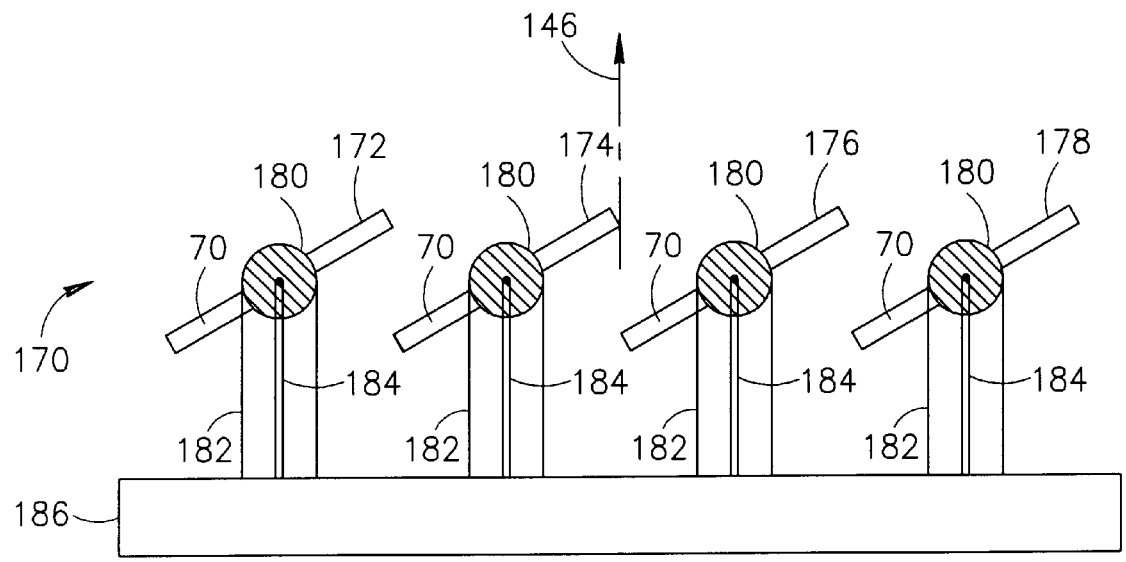

FIGS. 8A and 8B show still another preferred embodiment of the present invention, wherein a detector array 170 comprises a plurality of tiltable rows 172, 174, 176 and 178, each of which comprises a plurality of detector elements 70. Array 170 may be used in CT scanner 20 in place of detector array 30 shown in FIG. 1. Rows 172, 174, 176 and 178 have substantially equal widths. Each row is independently fixed to a pivot 180, which allows the row to tilt about a row axis substantially parallel to the row's long dimension. Preferably, pivots 180 are mounted on movable pivot mounts 184, and are rotated about the respective row axes by transmission belts 182, or other suitable rotation transmission devices. Mounts 184 and belts 182 are coupled to a motion control mechanism 186, which is preferably controlled by a computer, such as processor 88.

As shown in FIG. 8A, when rows 172, 174, 176 and 178 are oriented so as to define a plane that is substantially perpendicular to axis 146 (as described above), CT scanner 20 will produce four image slices having a common thickness, determined by the width of the rows. As FIG. 8B shows, however, when rows 172, 174, 176 and 178 are tilted, due to rotation of pivots 180, the thicknesses of the slices are reduced, as was described above with reference to FIG. 7B. Preferably all the rows are tilted by a common angle, so that the thicknesses of the slices are substantially equal.

Preferably, as shown in FIG. 8B, motion control mechanism 186 reduces the distance between mounts 184 when the rows are tilted. In this way, the slices may be maintained in substantial contiguity, i.e., without intervening spaces that are not imaged in between the image slices, regardless of changes in the thickness of the slices.

It will be appreciated that in the preferred embodiments of the present invention shown in FIGS. 7A, 7B, 8A and 8B and described above, image slices may be produced having substantially any desired thickness, by appropriately tilting the array or rows in the array, as long as the desired thickness is less than or equal to a maximum thickness, determined by the width of the rows of the array. Furthermore, although all the rows of array 150 in FIGS. 7A and 7B and of array 170 in FIGS. 8A and 8B are shown as having substantially equal widths, in other preferred embodiments of the invention, rows of different widths may be provided so as to produce slices of different thicknesses.

It will further be appreciated that in the preferred embodiment of the present invention shown in FIGS. 8A and 8B, the rows of array 170 need not all be tilted by an equal angle, as illustrated in FIG. 8B, but may rather be tilted by different angles, so as to produce slices of different thicknesses. Such varying slice thicknesses are useful in certain CT imaging modalities, for example, in CT imagining of the lungs, in which high- and low-resolution slices may be interspersed so as to reduce the radiation dose to which the body is exposed.

Furthermore, while tilting the detectors allows for a wide range of variation in the width of the slices, this range can be further increased by utilizing, in addition to such tilting, combination of rows as shown in FIGS. 4–6 and 9–11. One way these two methods could be combined is for the combination of rows to provide a first, coarser slice width and for the tilting to provide a finer variation on the combination width.

FIGS. 9A–9E show still another preferred embodiment of the present invention, wherein a detector array 190 has structure and function generally similar to those of arrays 30 and 102, and operates in conjunction with mechanical aperture 34, in a manner similar to that described above with reference to the preferred embodiment shown in FIGS. 5A–5D. The rows of array 190, however, have the following relative widths:

Central rows 198, 200—width=1
Rows 196, 202—width=1.5
Rows 194, 204—width=2.5
Rows 192, 206—width=5

Figure 9E:
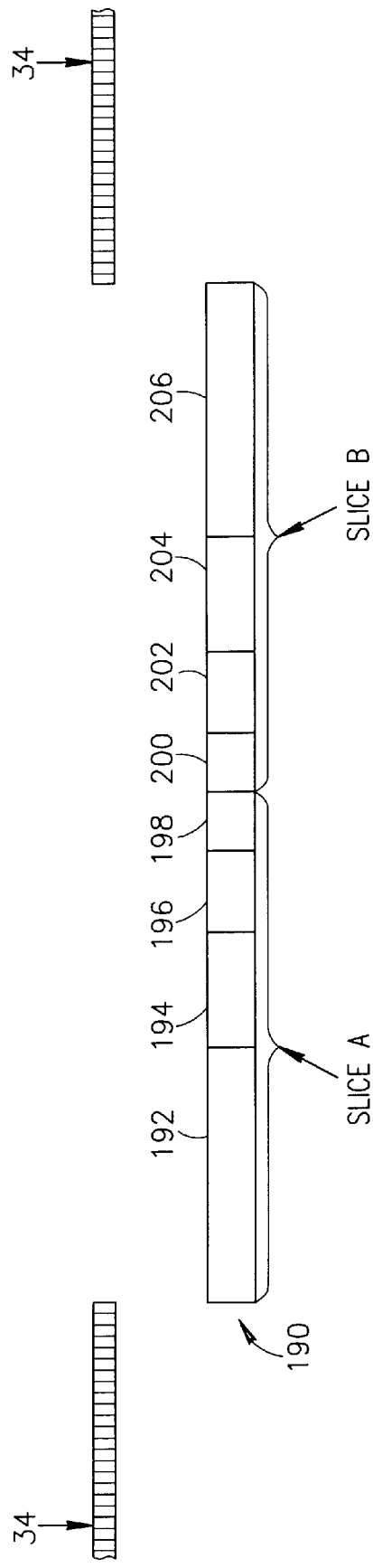
Figure 10:
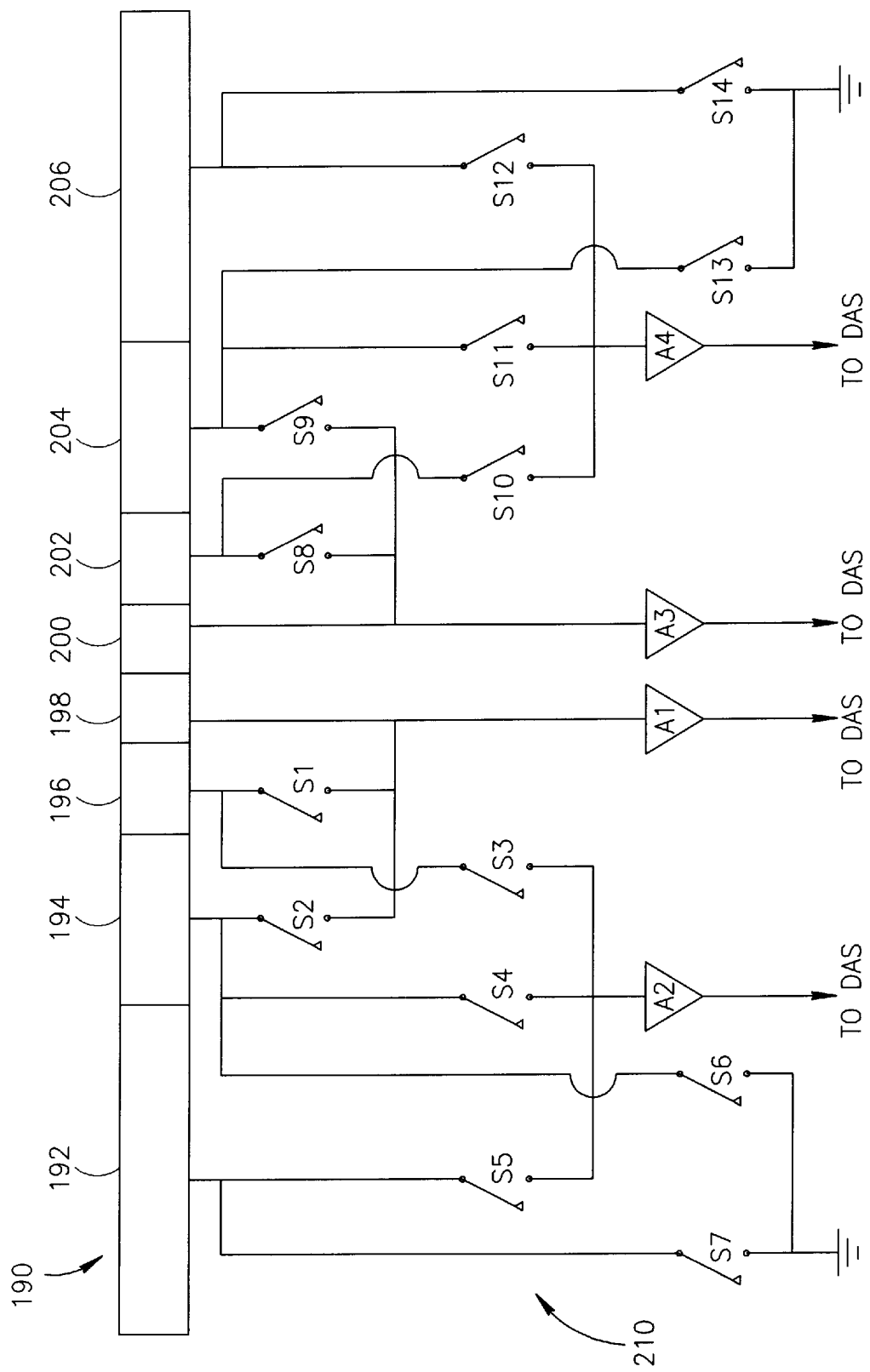
FIG. 10 is a schematic representation of switching circuitry associated with the detector array shown in FIGS. 9A–9E, in accordance with a preferred embodiment of the present invention.

FIG. 10 schematically shows a switching network 210 that receives signals from array 190 and selectively combines these signals to produce the slices shown in FIGS. 9A–9E. It will be appreciated that the network comprises two substantially identical and independent portions: a first portion coupled to rows 192, 194, 196 and 198, and a second portion coupled to rows 200, 202, 204 and 206. Network 210 is configured so that either two or four image slices may be simultaneously produced.

Thus, as shown in FIG. 9A, aperture 34 is narrowed laterally so as to mask substantially one half of the widths of rows 198 and 200, and the effective widths of these rows are then substantially equal to 0.5. Switches S1, S2, S8 and S9, shown in FIG. 10, are held in an open position, and two thin slices, A and B, are produced and acquired respectively by receiving an output from row 198 via adder A1 and an output from row 200 via adder A3. The remaining switches are closed, and the outputs of adders A2 and A4 are not used.

In FIG. 9B, aperture 34 is opened so that rows 198 and 200 are fully exposed, and substantially one third of the widths of rows 196 and 202 are masked, so that these rows have effective width=1. Switches S3, S6, S7, S10, S13 and S14 are closed, while the remaining switches are held open. Four slices having thickness corresponding to width=1 are thus produced and acquired via adders A1–A4.

In FIG. 9C, aperture 34 is opened still further, so as to expose substantially all of rows 194 and 204 (as well as rows 196, 198, 200 and 202 in between them). Switches S1, S4, S7, S8, S11 and S14 are closed, while the remaining switches are held open. The outputs of rows 196 and 198 are combined by adder A1, and those of rows 200 and 202, by adder A3. Four slices having thickness corresponding to effective row width=2.5 are thus produced and acquired via the adders.

In FIG. 9D, aperture 34 is fully open. Switches S1, S2, S5, S8, S9 and S12 are closed, while the remaining switches are held open. Four slices having thickness corresponding to effective row width=5 are thus produced.

Finally, FIG. 9E illustrates a configuration in which two slices, having thickness corresponding to effective row width=10, are produced. In this case, the switches are maintained in the same positions as were described above with reference to FIG. 9D. The outputs of adders A1 and A2 are combined, preferably by means of a software operation carried out by DAS 84, for example, to produce slice A, and the outputs of adders A3 and A4 are similarly combined to produce slice B.

It will thus be appreciated that array 190, having eight rows, together with switching network 210, is capable of producing two or four slices simultaneously, having an available range of five different slice thicknesses. Other preferred embodiments of the present invention, similar to that illustrated in FIGS. 9A–D and 10 but generally including detector arrays having a greater number of rows than array 190, can similarly produce more than four slices simultaneously.

Figure 11:
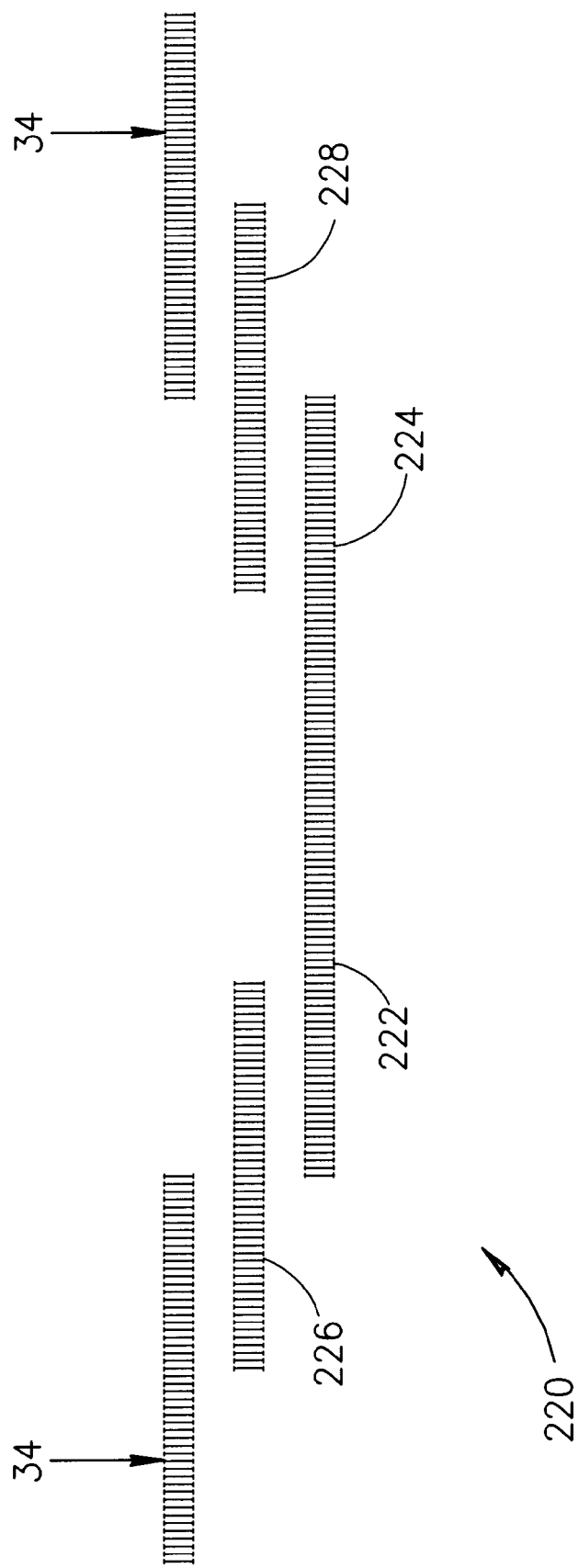
FIG. 11 is a schematic representation of a detector array and a mechanical aperture associated therewith, in accordance with still another preferred embodiment of the present invention.

FIG. 11 illustrates schematically yet another preferred embodiment of the present invention, in which a detector array 220 comprises four parallel rows of detectors: inner rows 222 and 224, and outer rows 226 and 228, each row corresponding to a respective image slice. Preferably all four rows have equal widths. As shown in the figure, outer rows 226 and 228 are mounted and positioned relative to inner rows 222 and 224 so that the outer rows may be translated laterally to overlap and mask portions of the widths of the inner rows. Preferably, aperture 34 and/or collimator 28 (as shown in FIG. 1) similarly masks portions of the widths of outer rows 226 and 228.

It will thus be appreciated that by translating rows 226 and 228 and correspondingly opening or closing aperture 34 (and/or collimator 28), the four image slices may be adjusted to substantially any desired thickness, up to a maximum corresponding to the full width of the rows. Preferably, outer rows 226 and 228 and aperture 34 and/or collimator 28 are positioned so that all four of the outer and inner rows have substantially equal effective widths. However, the principle described here of using one or more rows of the array to overlap and mask, and thus control the effective width of, one or more other rows, may similarly be used in other preferred embodiments of the present invention in which the array includes a greater or lesser number of rows, and produces image slices having equal or different thicknesses.

Although the above preferred embodiments have been described with reference to detector elements having substantially equal pitch sizes, wherein pitch is measured in a direction substantially parallel to long array axis 72, it will be appreciated that the principles of the present invention may similarly be applied to arrays of detectors having two or more different pitch sizes. Signals from adjacent detectors within a row of the array may also be combined, using switching circuitry and/or methods similar to those described above, or other circuitry and methods known in the art.

Figure 12:
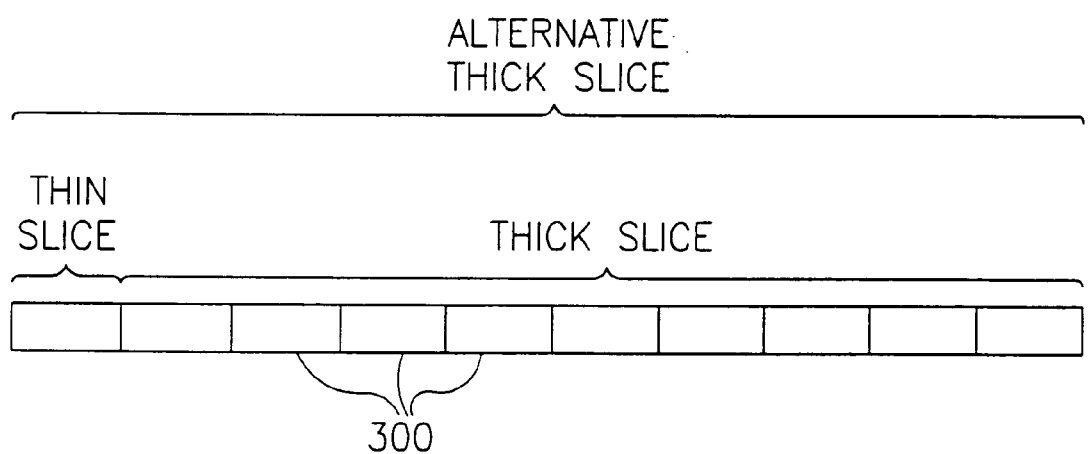
FIG. 12 shows two ways in which the outputs of detectors having the same width may be combined in accordance with a preferred embodiment of the invention.

FIG. 12 shows a first combination of detectors in different rows to produce composite slice widths especially suitable for lung imaging. In a preferred embodiment of the invention, 10 small detectors rows 300 each having a row width of 1–2 mm are utilized. In a preferred embodiment of the invention, the outputs of corresponding detectors in 9 of the rows are added together to form data for a thick slice while the data for the 10th row is used to form a thin slice. Alternatively, the outputs of all the rows are added together to form a thick slice and the outputs of one row is used to provide a thin slice. Alternatively, two thin slices may be provided in this manner, which thin slices can be either adjacent slices or formed of the outputs of rows at the ends of the group of rows. Further, alternatively, a single thin slice may be either at the center of the group of rows or at the edge of the group.

In a further alternative embodiment of the inventions non-uniform slices are produced using combinations of the outputs of detectors in non-uniform rows. In these embodiments for example, the row configurations of FIGS. 1, 2, 4, 5, 6 or 9 may be utilized. For example, in these configurations, signals from detectors in the two central thin rows may be combined to form a single relatively thin slice and signals from detectors in a plurality of adjacent outer detector rows may be combined to form two (or more) thick slices. These tin and thick slices may have any ratio, consistent with the available widths, but preferably a large ratio, as described above, is provided as required, for example, for lung images. Alternatively, two (or four) thin slices are provided utilizing the separate outputs of the detectors of the central two (or four) rows and thick slices are provided by summing the outputs of the detectors in the outside rows. Of course, if the ratio between the width of detectors in the various rows is large enough for the application, no summing is necessary.

Alternatively, only detectors on one side of the center of the row grouping are irradiated and only a single thin slice and a single thick slice is formed. Alternatively, the detectors on one side of the center line of the row configurations of FIGS. 1, 2, 4, 5, 6 or 9 may be omitted.

In a further preferred embodiment of the invention, a greater or lesser number of rows may be provided, such that the ratio between the slices is less then 9:1 or 10:1 described above. For example, if 6 equal rows are provided, then ratios of 6:1, 5:1 or less can be achieved. If a larger number of rows is provided, then more than one wide grouping of rows and more than one narrow grouping of rows may be achieved.

Preferred embodiments of the present invention have been described with reference to CT scanners and CT imaging of the human body, and are preferably used in the context of third- and fourth-generation CT scanners. The inventive principles of the present invention may be similarly applied, however, to CT scanners applied to industrial quality control and other applications, as well as to other imaging systems and methods.

It will be appreciated that the preferred embodiments described above are cited by way of example, and the full scope of the invention is limited only by the claims.

What is claimed is:

1. Apparatus for producing multiple image slice data responsive to incident radiation passing through an object, comprising;

a detector array comprising a plurality of parallel rows of detector elements, which receive said incident radiation and generates signals in response thereto, each of said rows being characterized by a row length and a detector width, measured in a direction perpendicular to the row length;

said detector width being measured without collimation;

signal processing circuitry which receives signals from said detector elements and which selectively combines the signals from one or more adjacent rows in one of a plurality of combination modes to form a plurality of group signals, said group signals representing the width of a slice, said slice width being different for each of said combination modes; and wherein the rows in the detector array having at least three substantially different detector widths.

2. Apparatus according to claim 1 wherein, for at least one combination mode, at least some of the groups comprises rows having different detector widths.

3. Apparatus according to claim 1 wherein for at least one combination mode, the combined widths of the rows making up each group are the same.

4. Apparatus according to claim 1 wherein for at least two of the combination modes, the number of groups is the same.

5. Apparatus in accordance with claim 1, wherein the groups of rows in each of said combination modes are mutually exclusive.

6. Apparatus in accordance with claim 1, wherein the signal processing circuitry comprises:

switching circuitry, which selects rows for inclusion in each of the n groups; and at least one adder, associated with one of the n groups, which sums the signals generated by a detector element in a first row of the group with signals generated by a detector element in at least one other row of the group.

7. Apparatus in accordance with claim 1, and comprising an adjustable slit or linear aperture, having an opening that is variable in a direction perpendicular to the long dimension of the rows, which may be variably closed to mask portions of the widths of the rows, wherein the effective group width is substantially equal to the sum of the widths of the rows in the group, less the portions of the widths of the rows in the group that are masked by the slit or aperture.

8. Apparatus in accordance with claim 7, and having a further mode of operation wherein the slit or aperture masks portions of the widths of two adjoining rows, and wherein the signal processing circuitry forms a set of two groups having substantially equal effective group widths, each said group comprising a respective on of said two adjoining rows.

9. Apparatus in accordance with claim 1, and comprising a movable base on which the detector array is mounted, which base moves the array in a direction perpendicular to the long dimension of the rows.

10. Apparatus in accordance with claim 1, wherein the detector array is planar in shape.

11. Apparatus in accordance with claim 1, wherein the detector array is arcuate in shape.

12. Apparatus for producing multiple image slice data responsive to incident radiation passing through an object, comprising:

a detector array comprising a plurality of parallel rows of detector elements, which receive said incident radiation and generates signals in response thereto, each of said rows being characterized by a row length and a detector width, measured in a direction perpendicular to the row length;

signal processing circuitry which receives signals from said detector elements and which selectively combines the signals from one or more adjacent rows in one of a plurality of combination modes to form a plurality of group signals, said group signals representing the width of a slice, said slice width being different for each of said combination modes;

wherein the rows in the detector array have at least three substantially different detector widths; and wherein the array includes two central rows having a common width smaller than or equal to the width of any of the other rows in the array.

13. Apparatus in accordance with claim 12, wherein the widths of all the rows are substantially integer multiples of the width of the central rows.

14. Apparatus in accordance with claim 12, wherein the array is symmetrical about a central axis, defined by a border between the two central rows, and wherein a third row peripherally adjoining one of the central rows has a width substantially equal to that of the two central rows, and wherein a fourth row peripherally adjoining the third row has a width twice that of the third row, and wherein a fifth row peripherally adjoining the fourth row has a width twice that of the fourth row.

15. Apparatus for producing multiple image data responsive to incident radiation passing through an object, comprising:

a detector array comprising a plurality of parallel rows of detector elements which receive said incident radiation and generate signals in response thereto, each of said rows being characterized by a row length and a detector width measured without collimation, measured in a direction perpendicular to the row length;

signal processing circuitry which receives signals from said detector elements and which selectively combines the signals from a plurality of adjacent rows in one of a plurality of combination modes to form a plurality of group signals, said group signals representing the width of the slice, said slice width being different for each of said combination modes; and wherein the plurality of rows that are combined to form the slice have at least two substantially different widths.

16. Apparatus for producing multiple image slice data responsive to incident radiation passing through an object, comprising:

a detector array comprising a plurality of parallel rows of detector elements which receive said incident radiation and generate signals in response thereto, each of said rows being characterized by a row length and a detector width measured in a direction perpendicular to the row length;

signal processing circuitry which receives signals from said detector elements and which selectively combines the signals from a plurality of adjacent rows in one of a plurality of combination modes to form a plurality of group signals, said group signals representing the width of a slice, said slice width being different for each of said combination modes;

wherein the plurality of rows that are combined to form a slice having at least two substantially different widths; and wherein the widths of at least two detector elements having substantially different widths are integral multiples of the width of the one of said at least two detector elements having the smallest width.

17. Apparatus in accordance with claim 16, and comprising an adjustable slit or linear aperture, having an opening that is variable in the lateral direction, which may be variably closed to mask portions of the widths of the detector elements, thereby varying the effective detector widths.

18. Apparatus in accordance with claim 16, and comprising a movable base on which the detector array is mounted, which base moves the array in the lateral direction.

19. Apparatus in accordance with claim 16, wherein the at least three detector elements comprise at least three substantially parallel rows of detector elements, said rows having a long dimension substantially perpendicular to the lateral direction and each row including a plurality of detector elements having a common width.

20. Apparatus for producing multiple image slice data responsive to incident radiation, comprising:

a detector array, comprising a plurality of parallel rows of detector elements, which generate signals responsive to radiation incident thereon, each of which rows is characterized by a width, measured in a direction perpendicular to a long dimension thereof; and signal processing circuitry, coupled to the array, which receives signals from at least four of the rows of the array, combines at least some signals from some of the rows, and produces four or more channels of output data, each such channel including data derived from signals generated by detector elements in one or more rows of the array selected by said circuitry, for inclusion of data therefrom in said channel, wherein each row is characterized by an effective row width, defined by a geometrical projection of the portion of the width of the row that is exposed to the radiation, onto a plane that is substantially perpendicular to a direction of propagation of the radiation incident on the array, and wherein each channel of output data is characterized by an effective channel width, defined by the sum of the effective widths of the one or more rows selected by the circuitry for inclusion of data therefrom in the channel, and wherein the effective channel widths of all of the four or more channels are substantially equal, and wherein the number of different effective channel widths that may be selected by the signal processing circuitry is equal to at least half the number of rows in the array, less one.

21. Apparatus in accordance with claim 20, wherein the signal processing circuitry comprises:

switching circuitry, which alternately selects different rows for inclusion of data therefrom in each of the four or more channels, thereby varying the effective channel widths thereof; and two or more adders, each respectively associated with one of the four or more channels, and each of which sums the signals generated by adjacent detectors in two or more respective, adjoining rows of the array that are selected by the circuitry for inclusion of data therefrom in the channel.

22. Apparatus for producing multiple image slice data responsive to incident radiation, comprising:

a detector array comprising a plurality of parallel rows of detector elements which generate signals responsive to radiation incident thereon, each of which rows is characterized by a width, measured in a direction perpendicular to a long dimension thereof;

signal processing circuitry coupled to the array which receives signals from at least four of the rows of the array, combines at least some of the signals for some of the rows and produces four or more channels of output data, each such channel including data derived from signals generated by detector elements in one or more rows the array selected by such circuitry, for inclusion of data therefrom in said channel;

wherein each row is characterized by an effective row width defined by a geometrical projection of the portion of the width of the row that is exposed to the radiation, onto a plane that is substantially perpendicular to a direction of propagation of the radiation incident on the array;

wherein each channel of output data is characterized by an effective channel width, defined by the sum of the effective widths of the one or more rows selected by the circuitry for inclusion of data therefrom in the channel;

wherein the effective channel widths of the four or more channels are substantially equal;

wherein the number of effective channel widths that may be selected by the signal processing circuitry is equal to at least half the number of rows in the array, less one;

wherein the array includes two central rows having a common width smaller than or equal to the widths of all the other rows; and wherein the widths of all the rows are substantially equal to integer multiples of the widths of the central rows.

23. Apparatus in accordance with claim 22, wherein the array is symmetrical about a central axis, defined by a border between the two central rows, and wherein a third row peripherally adjoining one of the central rows has a width substantially equal to that of the two central rows, and wherein a fourth row peripherally adjoining the third row has a width twice that of the third row, and wherein a fifth row peripherally adjoining the fourth row has a width twice that of the fourth row.

24. Apparatus in accordance with claim 22, and comprising an adjustable slit or linear aperture, having an aperture that is variable in a direction perpendicular to the long dimension of the rows, which may be variably closed to mask portions of the widths of the rows, thereby varying the effective row widths.

25. Apparatus in accordance with claim 24, wherein the plurality of parallel rows comprises eight parallel rows, and wherein the signal processing circuitry comprises fourteen switches, and produces four channels of output data of three different effective channel widths.

26. Apparatus in accordance with claim 22, wherein the array includes two central rows having a common width smaller than or equal to the widths of all the other rows, and wherein a third and a fourth row of the array that peripherally adjoin the two central rows on opposite sides of the two central rows have widths greater than the width of the central rows, and wherein the variable aperture masks portions of the widths of the third and fourth rows, so that the third and fourth rows have effective row widths substantially equal to the width of the two central rows, and wherein the four or more channels comprise four channels, and the signal processing circuit selects each one of the two central rows and the third and fourth rows for inclusion of data therefrom in one of the four channels.

27. Apparatus in accordance with claim 26, wherein the variable aperture masks portions of the widths of the two central rows, and the signal processing circuitry selects each one of the two central rows to produce two channels of output data having an effective width less than the width of the two central rows.

28. Apparatus in accordance with claim 24, and comprising a movable base on which the detector array is mounted, which base moves the array in a direction perpendicular to the long dimension of the rows.

29. Apparatus in accordance with claim 28, wherein the number of different effective channel widths that may be selected is greater than half the number of rows in the array.

30. Apparatus for producing multiple image slice data responsive to incident radiation, comprising:

a detector array comprising a plurality of parallel rows of detector elements, which generate signals responsive to radiation incident thereon, each of which rows is characterized by a width, measured in a direction perpendicular to a long dimension thereof;

signal processing circuitry coupled to the array, which receives signals from at least four of the rows of the array, combines at least some signals from some of the rows, and produces four or more channels of output data, each such channel including data derived from signals generated by detector elements in one or more rows of the array selected by said circuitry, for inclusion of data therefrom in said channel;

wherein each row is characterized by an effective row width, defined by a geometrical projection of the portion of the width of the row that is exposed to the radiation, onto a plane that is substantially perpendicular to a direction of propagation of the radiation incident on the array;

wherein each channel of output data is characterized by an effective channel width, defined by the sum of the effective widths of one or more rows selected by the circuitry for inclusion of data therefrom in the channel;

wherein the effective channel widths of all of the four or more channels are substantially equal;

wherein the number of different effective channels widths that may be selected by the signal processing circuitry is equal to at least half the number of rows in the array, less one;

wherein the four or more channels of output data comprise first, second, third and fourth channels, and wherein the first and second channels are combined, and the third and fourth channels are combined to produce two combined channels, each characterized by an effective channel width that is substantially equal to twice the effective channel widths of the four or more channels of output data.

31. Apparatus for producing multiple image slice data responsive to incident radiation comprising:

a detector array comprising a plurality of parallel rows of detector elements, which generate signals responsive to radiation incident thereon, each of which rows is characterized by a width measured in a direction perpendicular to a long dimension thereof;

signal processing circuitry coupled to the array which receives signals from at least four of the rows of the array, combines at least some signals from some of the rows, and produces four or more channels of output data, each such channel, including data derived from signals generated by detector elements of one or more rows of the array selected by the said circuitry, for inclusion of data therefrom in such channel;

wherein each row is characterized by an effective row width, defined by a geometrical projection of the portion of the width of the row that is exposed to the radiation, onto a plane that is substantially perpendicular to the direction of propagation of the radiation incident on the array;

wherein each channel of output data is characterized by an effective channel width defined by the sum of the effective widths of one or more rows selected by the circuitry for inclusion of data therefrom in the channel;

wherein the effective channel widths of all of the four or more channels are substantially equal;

wherein the number of different effective channel widths that may be selected by the signal processing circuitry is equal to at least half the number of rows in the array, less one;

wherein the array includes two central rows and further includes a third row and a fourth row that peripherally adjoin the two central rows on opposite sides of the two central rows; and wherein the third row and the fourth row are translated along a translation axis perpendicular to the long dimension of the rows so as to mask portions of the two central rows, thereby varying the effective widths of the two central rows.

32. Apparatus in accordance with claim 31, and comprising an adjustable slit or linear aperture, having an aperture that is variable in a direction perpendicular to the long dimension of the rows, which is variably closed to mask portions of the widths of the third and fourth rows of the array, thereby varying the effective widths of the third and fourth rows.

33. Apparatus in accordance with claim 31, wherein substantially any number of different effective channel widths may be selected.

34. Apparatus in accordance with claim 15, wherein the detector array is planar in shape.

35. Apparatus in accordance with claim 15, wherein the detector array is arcuate in shape.

36. Apparatus for producing multiple image slice data responsive to incident radiation, comprising:

a detector array comprising a plurality of parallel rows of detector elements, which generate signals responsive to radiation incident thereon, each of which rows is characterized by a width, measured in a direction perpendicular to a long dimension thereof;

signal processing circuitry coupled to the array which receives signals from at least four of the rows of the array, combines at least some signals from some of the rows, and produces four or more channels of output data, each such channel including data derived from signals generated by detector elements in one or more rows of the array selected by said circuitry, for inclusion of data therefrom in said channel;

wherein each row is characterized by an effective row width defined by geometrical projection of the portion of the width of the row that is exposed to the radiation onto a plane that is substantially perpendicular to the direction of propagation of the radiation incident on the array;

wherein each channel of output data is characterized by an effective channel width defined by the sum of the effective widths of one or more rows selected by the circuitry for inclusion of data therefrom in the channel;

wherein the effective channel widths of all four or more channels is substantially equal;

wherein the number of different effective channel widths that may be selected by the signal processing circuitry is equal to at least half the number of rows in the array less one; and wherein the apparatus comprises at least one mechanical tilting device which controllably tilts a row of the array about a tilt axis substantially parallel to the long dimension of the rows, wherein the effective row width is varied by controlling the at least one tilting device.

37. Apparatus in accordance with claim 36, wherein the at least one mechanical tilting device tilts all the rows of the array by a common angle.

38. Apparatus in accordance with claim 36, wherein the at least one mechanical tilting device tilts the entire array about a common axis.

39. Apparatus in accordance with claim 36, wherein the at least one mechanical tilting device comprises a plurality of such devices, which tilt about different, respective axes.

40. Apparatus in accordance with claim 39, wherein each row of the array is tilted about its own respective axis.

41. Apparatus in accordance with claim 39, and comprising a motion control mechanism, which controls a distance between adjoining rows of the array when they are tilted, so that geometrical projections of the rows onto the plane that is substantially perpendicular to the direction of propagation of the radiation incident on the array are substantially contiguous.

42. Apparatus in accordance with claim 36, wherein substantially any number of different effective channel widths may be located.

43. Apparatus in accordance with claim 1, and including one or more logarithmic amplifiers, to which signals generated by the detector elements are applied.

44. Apparatus in accordance with claim 43, wherein the one or more logarithmic amplifiers comprise a plurality of logarithmic amplifiers, each of which is coupled to a respective one of the detector elements.

45. Apparatus in accordance with claim 43, wherein the one or more logarithmic amplifiers receive output data from the signal processing circuitry.

46. Apparatus in accordance with claim 1, and including a data acquisition system, which receives the plurality of channels of output data.

47. Apparatus in accordance with claim 46, and including a reconstructor, which receives data from the data acquisition system and reconstructs a multiple-slice image therefrom.

48. Apparatus in accordance with claim 47, wherein the multiple-slice image comprises image slices, characterized by a variable slice thickness, and wherein the slice thickness is determined by the effective widths of the channels of output data.

49. Apparatus in accordance with claim 47, and including a display, which displays the multiple-slice image.

50. Apparatus in accordance with claim 49, and including a processor, which prints the multiple-slice image.

51. A CT scanner, for producing images of multiple sectional slices through an object, comprising:
    a radiation source (78), which irradiates the object from a first side thereof; and
    apparatus for producing image slice data in accordance with claim 1,
    wherein the detector array is positioned on a second side of the object, opposite to the first side.

52. A method for producing multiple-slice images of an object, comprising:
    irradiating the object;
    receiving and processing signals generated in response to radiation transmitted through a volume of the object;
    dividing the volume into a plurality of substantially contiguous, parallel object slices, each of which slices has a thickness approximately determined by the width of a respective detector that generates signals responsive to radiation transmitted therethrough;
    characterized in that it includes:
        producing two or more substantially contiguous sectional image slices having at least two different thicknesses, at least one such image slice corresponding to a plurality of adjoining object slices produced by combining raw signals relating to different slices; and
        reconstructing an image of the volume, said image including at least the two or more sectional image slices.

53. A method according to claim 52 wherein the width of the plurality of object slices is approximately the same.

54. A method according to claim 52 wherein the width of at least two of the object slices is different.

55. A method according to claim 52 wherein the thickness of the thickest reconstructed slice and the thickness of the thinnest image slice have a ratio of at least 3:1.

56. A method according to claim 52 wherein the ratio of the thickness of the image slices is at least 5:1.

57. A method according to claim 56 wherein the ratio of thicknesses of the image slices is at least 8:1.

58. A method according to claim 56 wherein the ratio of thicknesses of the image slices is about 10:1.

59. A method according to claim 52 wherein the image slices comprise a single thin slice and a single thick slice.

60. A method according to claim 52 wherein the image slices comprise a single thin slice and two thick slices.

61. A method according to claim 52 wherein the image slices comprise a single thick slice and two thin slices.

62. A method according to claim 52 wherein the image slices comprise two thick slices and two thin slices.

63. A method in accordance with claim 52, wherein receiving and processing signals comprises applying a log operation to the signals.

64. A method in accordance with claim 52, and comprising displaying the image of the volume.

65. A method in accordance with claim 52, and comprising printing the image of the volume.

* * * * *